United States Patent [19]

Horowitz et al.

[11] Patent Number: 5,712,086
[45] Date of Patent: Jan. 27, 1998

[54] PROCESS FOR TRANSFUSING CELL CONTAINING FRACTIONS STERILIZED WITH RADIATION AND A QUENCHER OF TYPE I AND TYPE II PHOTODYNAMIC REACTIONS

[75] Inventors: Bernard Horowitz, New Rochelle; Bolanle Williams, New York; Henrietta Margolis-Nunno, New York; Sing N. Chin, New York, all of N.Y.

[73] Assignee: New York Blood Center, Inc., New York, N.Y.

[21] Appl. No.: 486,668

[22] Filed: Jun. 7, 1995

Related U.S. Application Data

[62] Division of Ser. No. 364,031, Dec. 23, 1994, which is a continuation of Ser. No. 69,235, May 28, 1993, abandoned, which is a continuation-in-part of Ser. No. 31,787, Mar. 15, 1993, which is a division of Ser. No. 706,919, May 29, 1991, Pat. No. 5,232,844, which is a continuation-in-part of Ser. No. 524,208, May 15, 1990, Pat. No. 5,120,649.

[51] Int. Cl.$^6$ .................. A01N 1/02; C12N 13/00; A61M 37/00
[52] U.S. Cl. .................. 435/2; 435/173.1; 435/173.3; 604/4
[58] Field of Search .................. 604/4; 435/2, 173.3, 435/173.1

[56] References Cited

U.S. PATENT DOCUMENTS

| | | | |
|---|---|---|---|
| 4,008,136 | 2/1977 | Williams et al. | 210/748 |
| 4,049,798 | 9/1977 | Bottomley | 424/195.1 |
| 4,530,924 | 7/1985 | Polony et al. | 514/191 |
| 4,693,981 | 9/1987 | Wiesehahn et al. | 435/238 |
| 4,727,027 | 2/1988 | Wiesehahn et al. | 435/173.2 |
| 4,748,120 | 5/1988 | Wiesehahn | 435/173.3 |
| 4,775,625 | 10/1988 | Sieber | 435/238 |
| 4,791,062 | 12/1988 | Wiesehahn et al. | 435/238 |
| 4,878,891 | 11/1989 | Judy et al. | 604/5 |
| 4,935,498 | 6/1990 | Sessler et al. | 534/15 |
| 5,120,649 | 6/1992 | Horowitz | 435/173.3 |
| 5,232,844 | 8/1993 | Horowitz et al. | 435/173.1 |

FOREIGN PATENT DOCUMENTS

| | | |
|---|---|---|
| 0 066 886 | 12/1982 | European Pat. Off. . |
| 0 124 363 | 11/1984 | European Pat. Off. . |
| 88/10087 | 12/1988 | WIPO . |
| 89/11277 | 11/1989 | WIPO . |

OTHER PUBLICATIONS

A. Prince et al, *Eur. J. Epidemiol.*, 3: 103–118 (1987).
P. Mannucci et al, *The Lancet*, 782–785 (1988).
I. Rosenthal et al, *Phthalocyanines*, VCH Publishers, Inc., New York, 1989, pp. 393–425.
I. Rosenthal et al, *Cancer Lett.*, 30: 321–327 (1986).
Sonoda et al, *Photochem. Photobiol.*, 46: 625–531 (1987).
M. Cole et al, *Transfusion*, 29: Supp: 42s Abs. (1989).
K. Prodouz, *Transfusion*, 29: Supp: 42s Abs. (1989).
G. Moroff et al, *Transfusion*, 29: Supp: S15 Abs. (1989).
J. Matthews et al, *Transfusion*, 28: 81–83 (1988).
L. Lin et al, *Blood*, 74: 517–525 (1989).
B. Williams et al, *Blood*, 72: Supp: 287a (1988).
K. Prodouz et al, *Blood*, 70: 589–592 (1987).
F. Hartman et al, *Proc. Soc. Exp. Biol. Med.*, 70: 248–254 (1949).
G. LoGrippo et al, *Ann. N.Y. Acad. Sci.*, 83: 578–594.
J. Spikes, *Photochem. Photobiol.*, 43: 691–699 (1986).
E. Ben–Hur et al, *Int. J. Radiat. Biol.*, 47: 145–147 (1989).
A. Prince et al, *Thromb. Haemo.*, 44: 138–142 (1980).
B. Horowitz et al, *Transfusion*, 25: 516–522 (1985).
A. Prince et al, *J. Infectious Dis.*, 156: 268–272 (1987).
A. Prince et al, *PNAS USA*, 85: 6944–6948 (1988).
J. O'Brien et al, *J. Lab Clin. Med.*, 116: 439–447 (1990).
D. Gaffney et al, *Photochem. Photobiol.*, 53: 85–92 (1991).
T. Chanh et al, *J. Virol. Meth.*, 26: 125–132 (1989).
C. Lytle et al, *Photochem. Photobiol.*, 50: 367–371 (1989).
B. Horowitz et al, *Transfusion*, 31: 102–108 (1991).
Morgan et al, *Brit. J. Cancer*, 59: 366–70 (1989).
Snipes et al, *Radiat. Res.*, 70: 667 (1977).

*Primary Examiner*—Jon P. Weber
*Attorney, Agent, or Firm*—Sprung Horn Kramer & Woods

[57] ABSTRACT

A process is presented for transfusing cells which have been sterilized with radiation and a quencher of type I and type II photodynamic reactions. The cells are removed from a donor and exposed to virucidally effective amount of radiation in the presence of a quencher of type I and type II reactions, or a mixture of a quencher for type I reactions and a quencher of type II reactions. Subsequently, the sterilized cell containing fraction is returned to the donor.

48 Claims, 12 Drawing Sheets

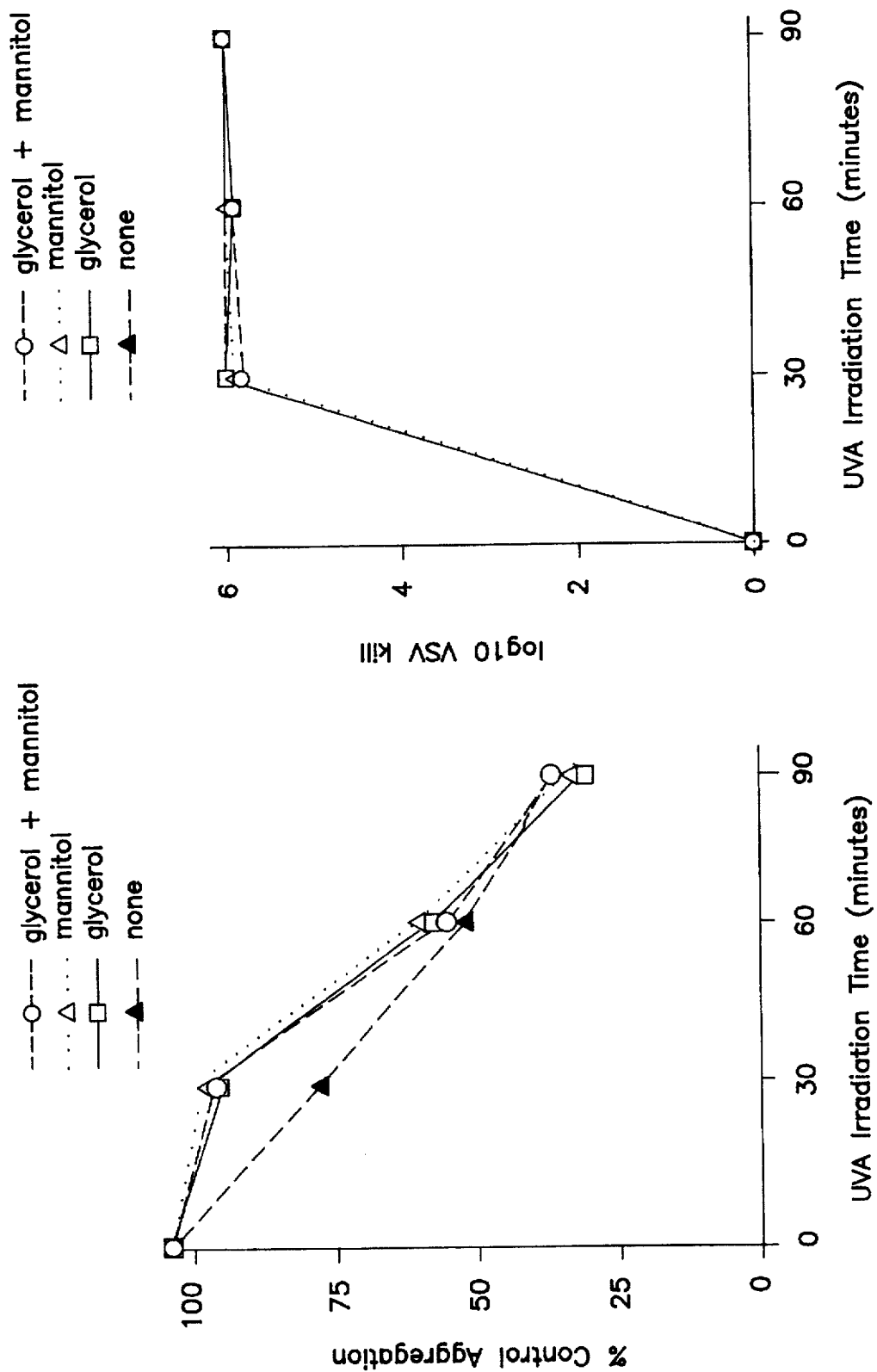

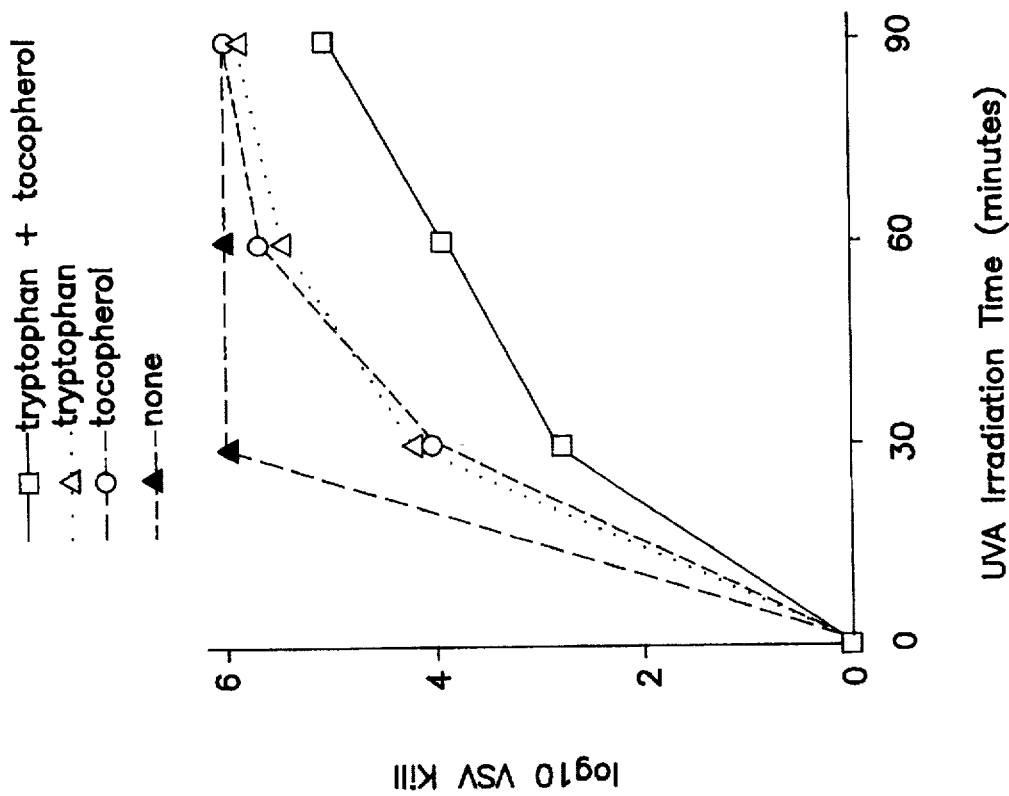
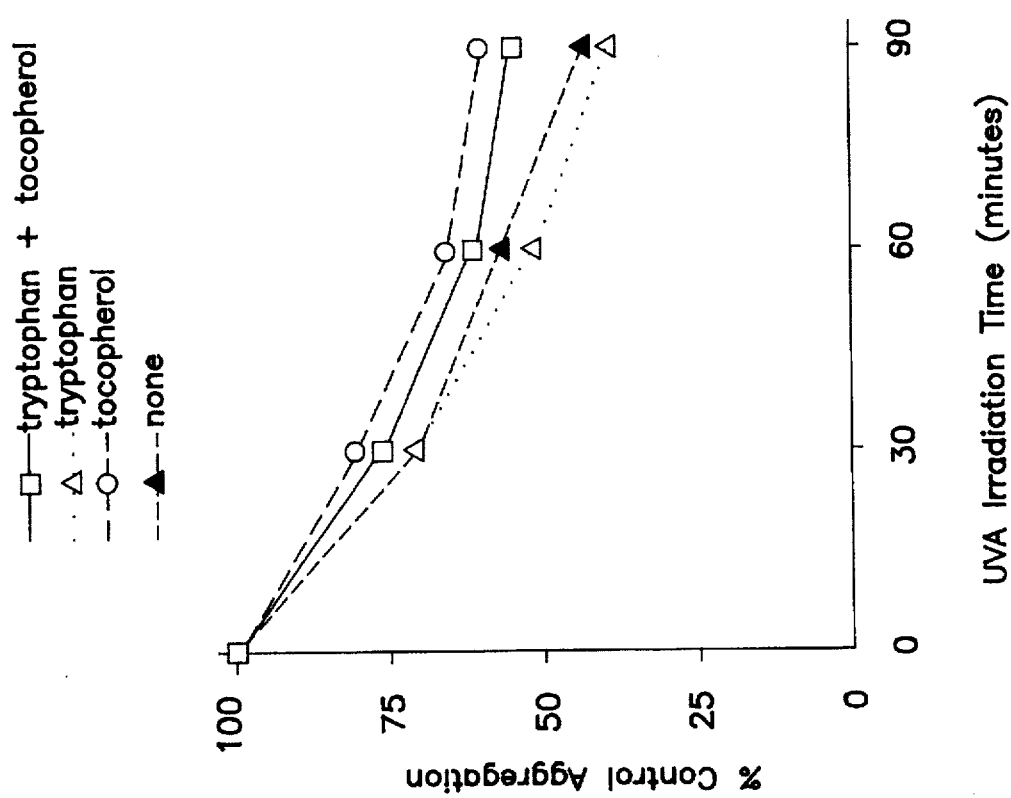
FIG. 2B
FIG. 2A

PROCESS FOR TRANSFUSING CELL CONTAINING FRACTIONS STERILIZED WITH RADIATION AND A QUENCHER OF TYPE I AND TYPE II PHOTODYNAMIC REACTIONS

This application is a divisional, of application Ser. No. 08/364,031, filed Dec. 23, 1994, now allowed, which is, in turn, a continuation of Ser. No. 08/069,235, filed May 28, 1993, now abandoned, which is, in turn, a continuation-in-part of U.S. Ser. No. 08/031,787, filed Mar. 15, 1993, which is, in turn, a divisional of U.S. Ser. No. 07/706,919, filed May 29, 1991, now U.S. Pat. No. 5,232,844, which is, in turn, a continuation-in-part of U.S. Ser. No. 07/524,208, filed May 15, 1990, now U.S. Pat. No. 5,120,649.

GOVERNMENT RIGHTS

This work is supported in part by award No. HL 41221 from the National Heart, Lung and Blood Institute.

BACKGROUND OF THE INVENTION

1. Field of the Invention

The present invention concerns a process for rendering a biological composition substantially free of enveloped and non-enveloped viruses contained therein without substantial disruption or inactivation of cells contained therein and without significant loss of labile proteins or other valuable biological components also contained therein.

2. Description of Related Art

The problems associated with the application of virucidal procedures to biological compositions and the efforts to date to overcome these problems, including the application of light and chemical agents is reviewed briefly in U.S. Pat. No. 5,120,649, the disclosure of which is incorporated herein by reference. See column 1, line 27, through column 4, line 41, therein.

Various photodynamic sterilization techniques have been evaluated for inactivating viruses in cellular components of blood. Although many of these appear promising for the treatment of red cell concentrates (Matthews et al., "Photodynamic therapy of viral contaminants with potential for blood banking applications", in *Transfusion*, 28:81–83 (1988); O'Brien et al., "Evaluation of merocyanine 540-sensitized photoirradiation as a means to inactivate enveloped viruses in blood products", in *J. Lab. Clin. Med.*, 116:439–47 (1990); and Horowitz et al., "Inactivation of viruses in blood with aluminum phthalocyanine derivatives", in *Transfusion*, 31:102–8 (1991)), photodynamic viral inactivation methods involving solely oxygen dependent reactions have so far proved inappropriate for the treatment of platelet concentrates (Proudouz et al., "Inhibition by albumin of merocyanine 540-mediated photosensitization of platelets and viruses", in *Transfusion*, 31:415–22 (1991), Dodd et al., "Inactivation of viruses in platelet suspensions that retain their in vitro characteristics: comparison of psoralen-ultraviolet A and merocyanine 540-visible light methods", in *Transfusion*, 31:483–90 (1991); and Horowitz et al., "Inactivation of viruses in red cell and platelet concentrates with aluminum phthalocyanine (AlPc) sulfonates", in *Blood Cells*, 18:141–50 (1992)).

One of the latest developments is the use of photoactive compounds. See, e.g., U.S. Pat. No. 5,120,649 and U.S. Ser. No. 07/706,919, filed May 29, 1991. Psoralen, together with UVA, has been shown to kill viruses in both cell-containing and cell-free solutions without undue damage to the valuable components needed for transfusion. Methylene blue, together with visible light, is being used to treat whole plasma. Phthalocyanines and other heme analogs, together with visible light, are being explored for treatment of red blood cell concentrates and other blood components.

Treatment with psoralens and long wavelength ultraviolet light (UVA) is known to produce various biochemical effects including oxygen independent interactions with nucleic acids (e.g., psoralen-DNA monoadduct formation and DNA crosslinking) and oxygen dependent reactions of a photodynamic nature (for review, see Gasparro, F. P. (Ed.) (1988) *Psoralen DNA Photobiology*, Vol I, Vol II, CRC Press, Boca Roton, Fla.). In contrast to the purely photodynamic procedures appropriate for red cells (above), the use of psoralens and UVA has demonstrated promise as a means of photo-inactivating viral contaminants in platelet concentrates, although in most studies (Lin et al., "Use of 8-methoxypsoralen and long-wavelength ultraviolet radiation for decontamination of platelet concentrates", in *Blood*, 74:517–525 (1989); and Dodd et al., supra, aminomethyl-trimethylpsoralen (AMT)), the combination of high levels of virus inactivation and the maintenance of platelet function were possible only when air was exchanged with nitrogen prior to UVA irradiation, a cumbersome procedure with inherent variability. However, it was recently demonstrated (Margolis-Nunno et al., "Virus Sterilization in Platelet Concentrates with Psoralen and UVA in the Presence of Quenchers" *Transfusion*, 22:541–547 (1992)), that for the inactivation of $\geq 6.0 \log_{10}$ cell-free vesicular stomatitis virus (VSV) by AMT and UVA, the need for oxygen depletion as a means of protecting platelets could be obviated by inclusion of mannitol, a scavenger (quencher) of free radicals. (The addition of quenchers of type I (free radical mediated) or of type II (singlet oxygen mediated) photodynamic reactions is frequently used in other contexts to distinguish which active oxygen species produces a particular photodynamic effect.) Under the conditions used in that study, i.e., 25 μg/ml AMT and 30 minutes of UVA with 2 mM mannitol, the inactivation of cell-free VSV in air was in part oxygen dependent since equivalent virus kill ($\geq 6.0 \log_{10}$) with oxygen depleted required 3 to 4 times more UVA irradiation time (90 minutes to 2 hours).

However, while these methods achieved a high level of kill of cell-free lipid enveloped viruses and of actively replicating, cell-associated virus, non-enveloped viruses and latent cell-associated viruses were not killed to a high extent under the conditions reported therein. Therefore, there was the need to effect the kill of these latter virus forms without causing significant damage to the desired, valuable components in the biological mixture. Conditions which result in the kill of $\geq 10^6$ infectious doses of latent or non-enveloped virus have been shown to modify red blood cells and platelets and result in compromised recovery of labile proteins such as factor VIII.

One of the most successful of the numerous methods developed to inactivate viruses in biological fluids is treatment with organic solvents and detergents; especially treatment with tri(n-butyl)phosphate (TNBP) and non-ionic detergents such as Tween 80 or Triton X-100. See, e.g., U.S. Pat. No. 4,540,573. This method results in excellent recovery of labile proteins, e.g., coagulation factor VIII and IX, while achieving a high level of virus kill, e.g., the killing of $\geq 10^6$ to $\geq 10^8$ ID, of enveloped viruses; however, little inactivation of non-enveloped viruses. See also, U.S. Pat. No. 4,481,189, wherein viral inactivation is by treatment with nonanionic detergent, alcohols, ethers, or mixtures thereof.

Other methods of virus inactivation commonly applied to biological fluids usable in a transfusion setting include treatment with heat at temperatures $\geq 60°$ C. or treatment with UVC together with B-propiolactone (B-PL). Each of these methods results either in a significant loss of labile proteins and/or incomplete virus killing. See, e.g., Horowitz, B., *Biotechnology of Blood*, "Inactivation of viruses found with plasma proteins", Goldstein, J., ed., Butterworth-Heinemann, Stoneham, 417–432, (1991). Additionally, adoption of B-PL has been slow because of its carcinogenicity. Newer methods intended to enhance virus safety are under development. The use of gamma irradiation has been explored in the laboratory, but, thus far, has not been used in the treatment of a commercially available product. See, Horowitz, B., et al., "Inactivation of viruses in labile blood derivatives 1. Disruption of lipid-enveloped viruses by tri (n-butyl)phosphate/detergent combinations", in *Transfusion*, 25:516–521 (1985); and Singer et al., "Preliminary Evaluation of Phthalocyanine Photosensitization For Inactivation Of Viral Pathogens in Blood Products", [abstract] *British J. Hematology*, March 23–25 (1988:Abs. 31). Filters are being developed which appear to remove $\geq 10^6$ ID$_{50}$ of each of several viruses; however, small viruses, e.g., parvovirus or Hepatitis A virus, would not be expected to be removed completely. Moreover, it is not known whether these filters can be commercially produced with the consistency needed for virus safety.

In spite of these advances, there continues to be a need for novel methods that achieve a high level of kill of both enveloped and non-enveloped viruses without significant loss of labile proteins or other valuable biological components.

SUMMARY OF THE INVENTION

The overall objective of the present invention was to achieve a high level of inactivation of both enveloped and non-enveloped viruses in biological compositions without incurring substantial disruption or inactivation of cells meant to be contained therein and without significant loss of labile proteins or other valuable biological components also contained therein. This objective was satisfied with the present invention, which relates generally to a process for inactivating extracellular and intracellular virus in a biological composition without incurring substantial disruption or inactivation thereof, said process comprising subjecting said composition to a virucidally effective amount of irradiation in the presence of (a) a mixture of a compound that quenches type I photodynamic reactions and a compound that quenches type II photodynamic reactions or (b) a bifunctional compound that is capable of quenching both type I and type II reactions, to thereby inactivate said virus while retaining functionality of said composition. The inventive process can, thus, be used to inactivate viruses in whole blood, red blood cell concentrates and platelet concentrates, without adversely affecting red blood cell or platelet structure or function. Similarly, the inventive process can be used to inactivate viruses in biological compositions without incurring substantial inactivation of desired, soluble biological substances (e.g., coagulation factor concentrates, hemoglobin solutions) contained therein.

In accordance with another aspect of the invention, the inventive process is advantageously carried out in the presence of an irradiation sensitizer compound.

In accordance with still another aspect of the invention, the inventive process is advantageously combined with a different virucidal method to enhance virus inactivation.

UV treatment alone of either plasma or AHF concentrates results in a relatively high loss of coagulation factor activity under conditions which kill $\geq 10^5$ ID$_{50}$ of virus; however, it has been discovered that this loss is significantly reduced (i.e., the recovery is high) when quenchers of photodynamic reactions are added prior to UV treatment. Compare, Murray et al., "Effect of ultraviolet radiation on the infectivity of icterogenic plasma", in *JAMA*, 157:8–14 (1955); and, more recently, Kallenbach et al., "Inactivation of viruses by ultraviolet light" in Morgenthaler J—J ed. "Virus inactivation in plasma products", in *Cum stud Hematol Blood Transfus.*, 56:70–82 (1989). Thus, the combined treatment according to the present invention results in a very high level of virus kill while coagulation factor activity is retained at high levels.

Gamma-irradiation of cellular components of blood is the technique of choice for the prevention of transfusion-associated (TA) graft-versus-host (GVHD) as is UVB irradiation of PCs for the prevention of HLA alloimmunization. However, some compromise of RBC (potassium leakage upon storage) and platelet (decreased bleeding time correction) integrity appear to be inherent with current irradiation protocols (Linden, J. V. and Pisciotto, P. 1992, "Transfusion associated graft-versus-host disease and blood irradiation," *Trans. Med. Rev.*, 6:116–123). The inclusion during τ-irradiation or UVB irradiation of quenchers (e.g., flavonoids) or quencher mixtures which scavenge both type I and type II photoreaction products will prevent damage to RBCs and platelets under conditions where WBCs are inactivated or otherwise altered. Recent reports of active oxygen species as the major contributors to potassium leakage and red cell membrane damage incurred with τ-irradiation (Anderson and Mintz, 1992; Sadrzadeh et al., 1992) support this theory and suggest that the addition of these quenchers will prevent K+ leakage by enhancing the nucleic acid specificity of this WBC inactivation procedure.

In addition, the use of τ-irradiation with quencher inclusion as an addition to viral envelope-directed virus sterilization procedures for RBCCs and PCs will assure latent virus or provirus inactivation in contaminating lymphocytes.

BRIEF DESCRIPTION OF THE DRAWINGS

FIG. 1 comprises four graphs depicting the results of the inactivation by AMT and UVA of VSV and bacteriophage M13 in the presence of mannitol, glycerol, or a mixture of mannitol and glycerol. FIG. 1a depicts the results for platelet function. FIG. 1b depicts the virus kill results for inactivation of cell-free VSV.

FIG. 2 comprises two graphs depicting the results of the inactivation of VSV by AMT and UVA in the presence of α-tocopherol phosphate, tryptophan, or a mixture of α-tocopherol and tryptophan. FIG. 2a depicts the results for platelet function. FIG. 2b depicts the virus kill results for VSV.

FIG. 3 comprises four graphs depicting the results of the inactivation of VSV and bacteriophage M13 by AMT and UVA in the presence of mannitol, α-tocopherol phosphate, or a mixture of mannitol and α-tocopherol phosphate.

FIG. 4 comprises two graphs depicting the results of the inactivation of VSV by AMT and UVA in the presence of quercetin or rutin or a mixture of α-tocopherol phosphate and mannitol.

FIG. 5 comprises two graphs depicting the results of the inactivation of VSV by AMT and UVA in the presence of quercetin or rutin or mannitol.

FIG. 9A depicts the results on the treatment of AHF concentrate. FIG. 9B depicts the results on the treatment of FFP.

DETAILED DESCRIPTION OF THE INVENTION

Figure 1D:
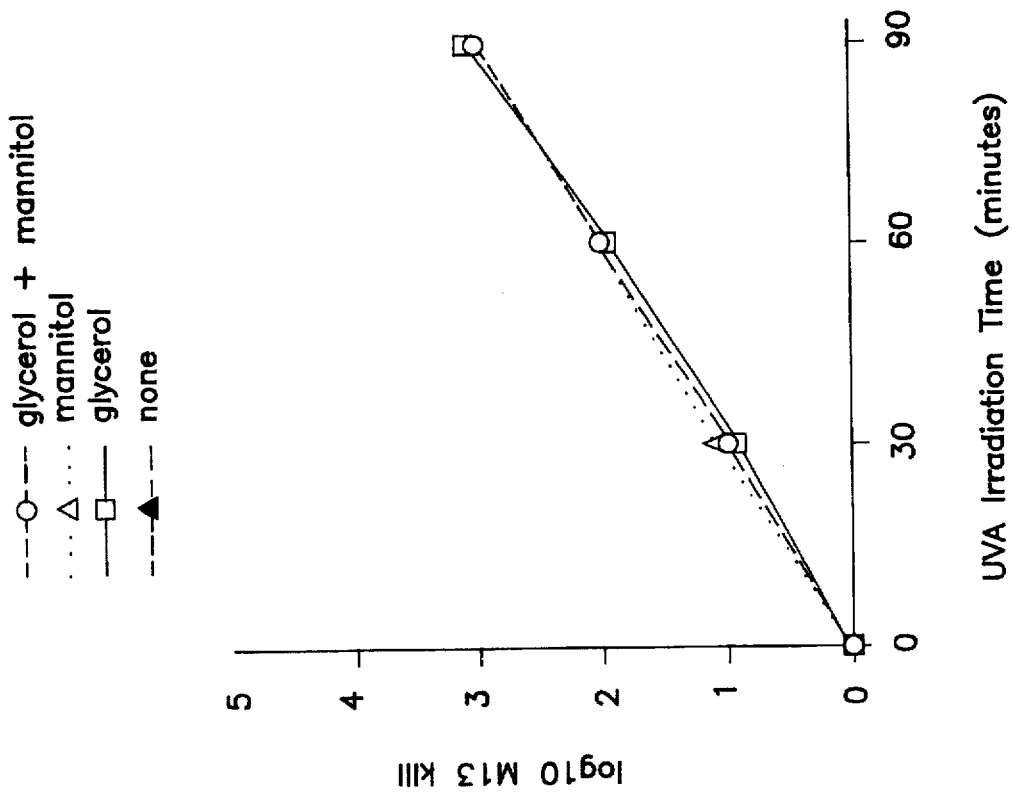
FIG. 1d depicts the virus kill results for bacteriophage M13.

Blood is made up of solids (cells, i.e., erythrocytes, leucocytes, and platelets) and liquid (plasma). The cells are transfused in the treatment of anemia, clotting disorders, infections, etc. In addition, the cells contain potentially valuable substances such as hemoglobin, and they can be induced to make other potentially valuable substances such as interferon, growth factors, and other biological response modifiers. The plasma is composed mainly of water, salts, lipids and proteins. The proteins are divided into groups called fibrinogen, serum globulins and serum albumin. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the cells and/or proteins to be concentrated, thus enhancing their therapeutic use.

Cell types found in human blood include red blood cells, platelets and several types of leukocytes. Methods for the preparation of cell concentrates useful in transfusion can be found in *Kirk Othmer's Encyclopedia of Chemical Technology*, Third Edition, Interscience Publishers, Volume 4, pp 25–37, the entire contents of which are incorporated by reference herein.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor—factor VIII, fibrin-stabilizing factor—factor XIII, fibrinogen), immunoglobins (immunoglobulins G, A, M, D, and E), and the complement components. There are currently more than 100 plasma proteins that have been described. A comprehensive listing can be found in "The Plasma Proteins", ed. Putnam, F. W., Academic Press, New York (1975).

Proteins found in the blood cell fraction include hemoglobin, fibronectin, fibrinogen, platelet derived growth factor, superoxide dismutase, enzymes of carbohydrate and protein metabolism, etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Academic Press, New York, (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromatographic processes. An excellent survey of blood fractionation also appears in *Kirk-Other's Encylopedia of Chemical Technology*, Third Edition, Interscience Publishers, Volume 4, pages 25 to 62, the entire contents of which are incorporated by reference herein.

The present invention is directed to subjecting a biological composition such as whole blood, red blood cell concentrates, platelet concentrates, platelet extracts, leukocyte concentrates, semen, ascites fluid, milk, lymphatic fluid, hybridoma cell lines and products derived from any of the above, to irradiation in the presence of a quencher or a mixture of quenchers.

The terms "cell-containing composition", "biological composition", or "biological fluid", as used herein, are not to be construed to include any living organism. Instead, the inventive method is intended to be carried out in an in vitro environment and the cell-containing composition, biological composition, or biological fluid obtained by the inventive method be an in vitro produced product, but will be usable in vivo.

The present invention can be employed to treat the product of a composition containing non-blood normal or cancerous cells or the product of gene splicing.

The term "irradiation" is to be construed broadly to include any form of radiation conventionally used to inactivate cells, e.g., white blood cells, or viruses, or parasites or other pathogenic organisms, e.g., *toxoplasma gondii, trypanosoma cruzi, plasmodium malariae*, or *babesia microti*, either alone or combined with some other agent or condition. Non-limiting examples of irradiation include UV (UVA, UVB, and UVC), gamma-irradiation, x-rays and visible light.

Details on the application of radiation to effect virus inactivation are well known to those skilled in the art. Typical radiation fluences range for the invention are 5–100 J/cm$^2$ (preferably 50–100 J/cm$^2$) for UVA, 0.02–2 J/cm$^2$ (preferably 0.05–0.2 J/cm$^2$) for UVC, and 1–40 kGy for τ irradiation. Surprisingly, it has now been discovered that virus inactivation can be advantageously enhanced if the conventional radiation treatment is carried out in the presence of a quencher or a mixture of quenchers.

Suitable quenchers of quencher mixtures are any substances known to react with both free radicals (so-called "type I quenchers") and reactive forms of oxygen (so-called "type II quenchers").

Representative quenchers include unsaturated fatty acids, reduced sugars, cholesterol, indole derivatives, and the like, azides, such as sodium azide, tryptophan, polyhydric alcohols such as glycerol and mannitol, thiols such as glutathione, superoxide dismutase, flavonoids, such as quercetin and rutin, amino acids, DABCO, vitamins and the like.

The quencher is used in conventional quenching amounts, but, surprisingly, when used, the overall process results in perferential damage to the virus but not the desired biological material.

In accordance with the present invention, superior virus kill is achieved by quenching both type I and type II photodynamic reactions, i.e., by using a mixture of type I and type II quenchers or by using compounds, e.g., flavonoids, that are known to quench both type I and type II reactions. The range of virus kill is in most cases broader than that achieved by using type I or type II quenchers alone—even as compared to increased concentrations of the type I or type II quencher—or by using mixtures of type I quenchers or mixtures of type II quenchers. Moreover, this broader range of virus kill is achieved without sacrificing intact cell functionality or structure.

Quenchers have been used previously to enhance reaction specificity in numerous systems, including X-irradiation and light activated compounds. However, the use of quenchers with UV treatment of biological fluids, especially blood protein solutions, has not been previously reported. U.S. Pat. No. 4,946,648, the disclosure of which is incorporated herein by reference, combines UV, solvents and detergents to treat virus spiked AHF or plasma, but the results are inferior to those achieved according to the present invention. The best treatment allowed for 5.4 logs of phage Kappa inactivation, accompanied by 74% of FVIII recovery. By way of contrast, one embodiment of the inventive process resulted in the inactivation of $\geqq 10^{16}$ $ID_{50}$ of VSV, a model enveloped virus, and $\geqq 10^{8}$ $ID_{50}$ of EMCV, a model non-enveloped virus, with FVIII recovery $\geqq 80\%$.

The inventive process is typically carried out over a temperature range of 0°–42° C., preferentially 20°–37° C. and most preferentially 20°–25° C. The inventive process is typically carried out at pH 6.5–8, most preferentially 7.2–7.6. Samples are typically subjected to the inventive process for a period of time of less than 24 hours; preferentially less than 4 hours for $\tau$ or X-irradiation. Samples can also be treated frozen.

In an embodiment of the present invention, the biological composition is subjected to irradiation and the quencher or quencher mixture in the presence of an irradiation sensitizer. In this context, suitable irradiation sensitizer compounds for use in the present invention include phthalocyanines, purpurins, and other molecules which resemble the porphyrins in structure (as described above) as well as photoactive compounds excited by ultraviolet light (e.g., psoralen, 8-methoxypsoralen, 4'-aminomethyl-4,5', 8-trimethyl psoralen, bergapten, and angelicin), dyes which absorb light in the visible spectrum (e.g., hypericin, methylene blue, eosin, fluoresceins and flavins), and dyes which absorb X-irradiation (e.g. brominated psoralen, brominated hematoporphyrin, iodinated phthalocyanine). The use of such irradiation sensitizers would be readily apparent to those skilled in the art and is preferably substantially as described in U.S. Pat. No. 5,120,649 and U.S. Ser. No. 07/706,919, filed May 29, 1991, the disclosures of which are incorporated herein by reference.

According to another embodiment of the invention, the treatment of the biological composition with irradiation and quencher or quencher mixture is combined with a second virucidal method. This second virucidal method can be any method used conventionally to inactivate enveloped and/or non-enveloped viruses such as, merely for example, heat treatment, dry or otherwise, pH manipulation, treatment with lipid solvents and/or detergents, a separate irradiation treatment, e.g., with gamma-irradiation, or treatment with chemical agents, e.g., formaldehyde.

In a preferred embodiment, the second virucidal method is a solvent/detergent treatment such as that disclosed in U.S. Pat. No. 4,540,573, the disclosure of which is hereby incorporated by reference. In this embodiment, the biological fluid is contacted with a dialkylphosphate or a trialkylphosphate having alkyl groups which contain 1 to 10 carbon atoms, especially 2 to 10 carbon atoms. Illustrative members of trialkylphosphates for use in the present invention include tri-(n-butyl) phosphate, tri-(t-butyl) phosphate, tri-(n-hexyl) phosphate, tri-(2-ethylhexyl) phosphate, and tri (n-decyl) phosphate, just to name a few. An especially preferred trialkylphosphate is tri-(n-butyl) phosphate. Mixtures of different trialkylphosphates can also be employed as well as phosphates having alkyl groups of different alkyl chains, for example, ethyl di(n-butyl) phosphate. Similarly, the respective dialkylphosphates can be employed including those of different alkyl group mixtures of dialkylphosphate. Furthermore, mixtures of di- and trialkylphosphates can be employed.

Di- or trialkylphosphates for use in the present invention are employed in an amount between about 0.01 mg/ml and about 100 mg/ml, and preferably between about 0.1 mg/ml and about 10 mg/ml.

The di- or trialkylphosphate can be used with or without the addition of wetting agents. It is preferred, however, to use di- or trialkylphosphate in conjunction with a wetting agent. Such wetting agent can be added either before, simultaneously with or after the di- or trialkylphosphate contacts the biological fluid. The function of the wetting agent is to enhance the contact of the virus in the biological fluid with the di- or trialkylphosphate. The wetting agent alone does not adequately inactivate the virus.

Preferred wetting agents are non-toxic detergents. Contemplated nonionic detergents include those which disperse at the prevailing temperature at least 0.1% by weight of the fat in an aqueous solution containing the same when 1 gram detergent per 100 ml of solution is introduced therein. In particular there is contemplated detergents which include polyoxyethylene derivatives of fatty acids, partial esters of sorbitol anhydrides, for example, those products known commercially as "Tween 80", "Tween 20" and "polysorbate 80" and nonionic oil soluble water detergents such as that sold commercially under the trademark "Triton X 100" (oxyethylated alkylphenol). Also contemplated is sodium deoxycholate as well as the "Zwittergents" which are synthetic zwitterionic detergents known as "sulfobetaines" such as N-dodecyl-N, N-dimethyl-2-ammonio-1-ethane sulphonate and its congeners or non-ionic detergents such as octyl-beta-D-glucopyranoside.

The amount of wetting agent, if employed, is not crucial; for example, from about 0.001% to about 10%, preferably about 0.01 to 1.5%, can be used.

Di- and trialkylphosphates may be used in conjunction with other inactivating agents such as alcohol or ethers with or without the copresence of wetting agents in accordance with U.S. Pat. No. 4,481,189, the disclosure of which is incorporated by reference herein.

Treatment of biological fluids with trialkylphosphate is effected at a temperature between −5° C. and 70° C., preferably between 0° C. and 60° C. The time of such treatment (contact) is for at least 1 minute, preferably at least 1 hour and generally 4 to 24 hours. The treatment is normally effected at atmospheric pressure, although subatmospheric and superatmospheric pressures can also be employed.

Normally, after the treatment, the trialkylphosphate and other inactivating agents, for example, ether, are removed, although such is not necessary in all instances, depending upon the nature of the virus inactivating agents and the intended further processing of the biological fluid.

Di- or trialkylphosphate and non-ionic detergents can be removed as follows:

(1) extraction with physiologically compatible oils (U.S. Pat. No. 4,789,545);

(2) diafiltration using ether insoluble, e.g. "TEFLON", microporous membranes which retain the plasma proteins;

(3) absorption of desired plasma components on chromatographic or affinity chromographic supports; and (4) precipitation, for example, by salting out of plasma proteins.

In particular, removal from AHF can be effected by precipitation of AHF with 2.2 molal glycine and 2.0M sodium chloride. Removal from fibronectin can be effected by binding the fibronectin on a column of insolubilized gelatin and washing the bound fibronectin free of reagent.

Non-limiting examples of lipid coated, human pathogenic viruses that can be inactivated by the present invention include vesicular stomatitis virus (VSV), Moloney sarcoma virus, Sindbis virus, human immunodeficiency viruses (HIV-1; HIV-2), human T-cell lymphotorophic virus-I (HTLV-I), hepatitis B virus, non-A, non-B hepatitis virus (NANB) (hepatitis C), cytomegalovirus, Epstein Barr viruses, lactate dehydrogenase elevating virus, herpes group viruses, rhabdoviruses, leukoviruses, myxoviruses, alphaviruses, Arboviruses (group B), paramyxoviruses, arenaviruses and coronaviruses. Non-limiting examples of non-enveloped viruses that can be inactivated by the present invention include parvovirus, polio virus, hepatitis A virus, enteric non-A, non-B hepatitis virus, bacteriophage M13 and satellite adeno-associated virus (AAV).

Cell-containing compositions to be treated according to the invention have $\geq 1 \times 10^8$ cells/ml, preferably $\geq 1 \times 10^9$ cells/ml and most preferably $\geq 1 \times 10^{10}$ cells/ml. Furthermore, cell-containing compositions to be treated according to the invention have preferably >4 mg/ml protein and more preferably >25 mg/ml protein and most preferably 50 to 60 mg/ml protein (unwashed cells).

Non-cell containing compositions to be treated according to the invention have $\geq 0.1$ mg/ml and preferably $\geq 5$ mg/ml protein.

In the inventive process, at least $10^4$, preferably $10^6$, infectious units of virus parasite or other pathogen are inactivated.

The biological compositions treated according to the invention, while initially containing $\geq 1000$ infectious units of virus/L, after the virus has been inactivated and treatment according to the invention has been conducted, have, in the case of cell-containing compositions, a retention of intact cell functionality and structure of greater than 70%, preferably greater than 80% and most preferably greater than 95%. In the case of biological fluids, a retention of biological activity of greater than 75%, preferably greater than 85%, and most preferably greater than 95% can be achieved.

By the inactivation procedure of the invention, most if not virtually all of the viruses contained therein would be inactivated. A method for determining infectivity levels by inoculation into chimpanzees (in vivo) is discussed by Prince, A. M., Stephen, W., Bortman, B. and van den Ende, M. C., "Evaluation of the Effect of Beta-propiolactone/Ultraviolet Irradiation (BPL/UV) Treatment of Source Plasma on Hepatitis Transmission by Factor IX Complex in Chimpanzees", *Thrombosis and Hemostasis*, 44:138–142, (1980).

According to the invention, inactivation of virus is obtained to the extent of at least "4 logs", preferably $\geq 6$ logs, i.e., virus in the sample is totally inactivated to the extent determined by infectivity studies where that virus is present in the untreated sample in such a concentration that even after dilution to $10^4$ (or $10^6$), viral activity can be measured.

The present invention describes inactivating viruses, while simultaneously retaining labile blood cell functional and structural features.

Functional activities of platelets are determined by their ability to aggregate in the presence of certain biological agents and their morphology. Structural integrity of platelets is assessed by in vivo survival following radiolabeling with indium-111 and identification of the presence of specific platelet antigens.

After treatment with the photoreactive compound, excess photoreactive compound can be removed by centrifugation, washing dialysis, and/or adsorption onto hydrophobic matrices.

In an embodiment of the present invention, the treated cell-containing fraction from the inventive process is transfused or returned to the donor, e.g., human donor, from which the initial cell-containing fraction was derived. In this manner, the level of circulating virus in the donor will be reduced, thus improving the donor's ability to clear virus and/or improving the efficacy of antiviral drugs.

Factor VIII and factor IX coagulant activities are assayed by determining the degree of correction in APTT time of factor VIII—and factor IX—deficient plasma, respectively. J. G. Lenahan, Philips and Philips, *Clin. Chem.*, Vol. 12, page 269 (1966).

The activity of proteins which are enzymes is determined by measuring their enzymatic activity. Factor IX's activity can be measured by that technique.

Binding proteins can have their activities measured by determining their kinetics and affinity of binding to their natural substrates.

Lymphokine activity is measured biologically in cell systems, typically by assaying their biological activity in cell cultures.

Protein activity generally is determined by the known and standard modes for determining the activity of the protein or type of protein involved.

The invention will now be described with reference to the following non-limiting examples.

EXAMPLES

Materials and Methods

Blood

Whole blood was typically less than 48 hours old when used. Prior to use, it was stored at 4° C.

Platelet Concentrates (PCs)

PCs, released after routine blood bank testing, were typically 24 to 48 hours old when treated. Prior to treatment, the PCs were stored at 22° to 24° C. in the bags (PL 732, Fenwal Laboratories, Deerfield, Ill.) in which they were received and constantly agitated on a platelet rotator (Helmer Labs, St. Paul, Minn.).

Psoralen Solutions

4'-aminomethyl-4,5',8-trimethylpsoralen (AMT) was purchased from HRI Assoc. Inc., Concord, Calif. Stock solutions of AMT (4 mg/ml) were prepared in distilled water.

Model Virus Studies

The inactivation of the following viruses was studied: vesicular stomatitis virus (VSV), a lipid enveloped, RNA virus; encephalomyocarditis virus (EMC), a protein enveloped, RNA virus; human immunodeficiency virus (HIV), a human, pathogenic retrovirus; hepatitis A virus, a non-enveloped, RNA virus; adeno-associated virus, a non-enveloped, DNA virus; M13, a non-enveloped bacteriophage; and poliovirus, a non-enveloped, RNA virus.

The pHM175 strain of HAV was propagated in monolayer cultures of African green monkey kidney (BS-C-1) cells as described by Jansen et al, 1988 (Jansen R. W., J. E. Newbold and S. M. Lemon, *Virology*, 163:299–307, 1988).

Quantitation of viral infectivity was based on the autoradiographic detection of foci developed in cell sheets maintained beneath 0.5% agarose overlays following fixation of cells with 80% acetone and subsequent staining with I-125 labelled antibody (IgG) to HAV.

Ten fold serial dilutions of HAV in MEM culture medium supplemented with 2% fetal calf serum were prepared; each dilution was used to inoculate duplicate 60 mm Corning dishes of BS-C-1 cells. After 5–7 days incubation at 35 degrees Centigrade in a humidified environment with 5% $CO_2$, foci derived from individual virus particle replication were visualized, enumerated and results were expressed in terms of radioimmunofocus forming units (RFU) of virus.

Subconfluent 293 cells were co-infected with 10 PFU of Ad5, and 10-fold serial dilutions of AAV in DMEM supplemented with 2% fetal calf serum in 24 well plates. At 48 hours post infection and incubation at 37° C. in a humidified environment with 5% $CO_2$, the cells were scraped from the wells, washed, denatured and hybridized to an AAV ($_{32}P$) DNA probe and autoradiography as described by Carter et al, *Virology*, 128:505–516, 1983, was carried out. Following exposure to X-ray film and counting, cpm standard curves were drawn from the known virus stock and used to determine the concentration of AAV in each dilution of the unknown sample.

VSV was cultured in human A549 cells. EMC stocks were prepared in mouse L929 or human A459 cells. Poliovirus was grown in human HeLa cells. Culturing and assay procedures were similar to those described in Horowitz, B., Wiebe, M. E., Lippin, A. and Stryker, M. H., "Inactivation of Viruses in Labile Blood Derivatives", *Transfusion*, 1985; 25:516–522. Infectivity of VSV, EMC and poliovirus was assessed by endpoint, 10-fold serial dilutions in DMEM culture medium (Gibco Laboratories, Grand Island, N.Y.) with 10% fetal calf serum (FCS; MA Bioproducts, Walkersville, Md.). Each dilution was used to inoculate eight replicate wells of human A549 (VSV or EMC) or HeLa (poliovirus) cells in 96-well microtiter plates. Virus-induced cytopathology was scored after 72 hours of incubation at 37° C. in 5% $CO_2$. The reported virus titer was calculated using the Spearman-Karber method (Spearman, C., "The Method of Right and Wrong Cases' ('Constant Stimuli') Without Gauss's Formula", *Br. J. Psychol.*, 1908; 2:227–242) and indicates the quantity of virus which infects 50% of the tissue culture wells ($TCID_{50}$).

Cell-associated VSV was prepared by incubating a confluent monolayer of human A549 cells with 5 ml of $10^7$ $ID_{50}$/ml VSV in serum-free DMEM for 1 hour at 37° C. under 5% $CO_2$ in 150 cm$^2$ tissue culture flasks. The multiplicity of infection under these conditions was approximately 2.1 $TCID_{50}$/cell. After decanting off the liquid, the attached cells were washed three times to remove free virus with 50 ml PBS per wash. Afterwards, 40 ml of DMEM containing 5% FCS were added, and the cells were incubated for an additional 4¾ hours. The attached cells were washed three times with PBS and released by treatment for 10 minutes with a normal saline solution containing 0.01% trypsin (Cooper Biomedical, Freehold, N.J.; two times crystallized) and 5 µg/ml EDTA. The released cells were collected by centrifugation, washed three times with PBS and resuspended in PBS.

For assessment of virus inactivation, the virucidal reaction was stopped by 10-fold dilution into DMEM containing 5% fetal calf serum, and the cells when present were removed by centrifugation at 1500 rpm for 10 minutes. The lack of virus inactivation at this dilution or in the absence of irradiation was confirmed for each of the inactivation conditions studied. Samples were sterile filtered (Swinnex filters, Millipore Corp., Bedford, Mass.) and frozen at −70° C. or below until assay.

The procedures for the assessment of the inactivation of cell-associated VSV were similar to those of cell-free VSV, except all experiments with cell-associated VSV were carried out under totally controlled aseptic conditions. At the conclusion of the experiment, the infected A549 cells were isolated by centrifugation, washed three times with PBS by centrifugation, resuspended in 1 ml PBS and immediately assayed for VSV infectivity by endpoint, 10-fold serial dilutions as with cell-free virus.

Example 1: Effect of inclusion of type I quenchers during treatment of a platelet concentrate with AMT and UVA Aliquots (3 ml) from a platelet concentrate were treated with 25 µg/ml of 4'-aminomethyl-4,5',8-trimethylpsoralen (AMT) and 7.5 mW/cm$^2$ UVA for the times indicated in the presence or absence of various type I quenchers. Prior to treatment, cell-free vesicular stomatitis virus (VSV), cell-associated VSV, or the non-enveloped bacteriophage M13 were added separately to platelet concentrate aliquots. Following treatment, samples containing virus were assayed for viral infectivity and samples without virus were stored overnight and then assayed for aggregation in response to 20 µg/ml collagen in a BioData aggregometer. The aggregation response provided in the table compares the initial rate of aggregation in the treated sample to that observed in the untreated control.

The results of Example 1, shown in Table I, indicate that with the 30 minute UVA irradiation time necessary for the complete inactivation of cell-free VSV ($\geq 6.0 \log_{10}$) by AMT, the addition of certain type I quenchers (e.g., 2 mM mannitol, 4 mM glycerol) improved platelet aggregation function from about 70% to more than 90% of control levels. There was, however, little inactivation of cell-associated VSV or of M13 with 30 minute treatment, whether or not type I quenchers were present. With the UVA irradiation times of 60 minutes or more that were required for more than 1 $\log_{10}$ kill of cell-associated or non-enveloped virus, platelet function was sacrificed (the rate of aggregation was 60% or less, even in the presence of type I quenchers at concentrations of up to 50 mM).

The data in Table I also indicate that the inclusion of type I quenchers, at concentrations of up to at least 10 mM, had no apparent effect on the inactivation of cell-free or cell-associated VSV or of M13 by AMT and UVA.

TABLE I

Addition of Type I Quenchers: Effects on Platelet Aggregation and Virus Kill.

| Quencher (Concentration) | Aggregation Response % Control | | | Virus Inactivation $(\log_{10})^{(3)}$ | | |
|---|---|---|---|---|---|---|
| | $30^{(1)}$ | 60 | 90 | Cell-Free VSV | Cell-Associated VSV | M13 |
| Mannitol (2 mM) | 95 | 60 | 32 | $\geq 6.0$ | $1, 2^{(4)}, 3^{(5)}$ | $1, 2^{(4)}, 3^{(5)}$ |
| Mannitol (4 mM) | 95 | 58 | n.a$^{(2)}$ | $\geq 6.0$ | | |
| Mannitol (10 mM) | 91 | 56 | n.a | $\geq 6.0$ | $1, 2^{(4)}, 3^{(5)}$ | |
| Mannitol) (50 mM) | 85 | 55 | 30 | 5.8 | | |
| Glycerol (2 mM) | 90 | 50 | n.a. | $\geq 6.0$ | | |
| Glycerol (4 mM) | 95 | 55 | 35 | $\geq 6.0$ | $1, 2^{(4)}, 3^{(5)}$ | $1, 2^{(4)}, 3^{(5)}$ |
| Glycerol (10 mM) | 80 | 50 | n.a. | $\geq 6.0$ | | |
| Glycerol (50 mM) | 85 | 50 | n.a. | 5.8 | | |
| Glutathione (2 mM) | 80 | 60 | 40 | $\geq 6.0$ | | |
| Glutathione (4 mM) | 80 | 55 | 25 | $\geq 6.0$ | | |
| Glutathione (10 mM) | 75 | n.a. | n.a. | $\geq 6.0$ | | |
| Superoxide Dismutase (20 µg/ml) | 85 | 50 | 30 | $\geq 6.0$ | | |
| Superoxide Dismutase (100 µg/ml) | 75 | 45 | n.a. | n.a. | | |
| none (—) | 75 | 52 | 35 | $\geq 6.0$ | $1, 2^{(4)}, 3^{(5)}$ | $1, 2^{(4)}, 3^{(5)}$ |

$^{(1)}$minutes UVA exposure;
$^{(2)}$n.a. = not available;
$^{(3)}$Unless otherwise indicated only virus results with 30 min. UVA are provided since longer treatment times compromised platelet integrity;
$^{(4)}$Kill results with 60 minutes UVA;
$^{(5)}$Kill results with 90 minutes UVA.

Example 2. Effect of inclusion of type II quenchers during treatment of a platelet concentrate with AMT and UVA A platelet concentrate (3 ml) was treated with 25 µg/ml AMT and 11 mW/cm² UVA for the times indicated, in the presence or absence of various type II quenchers. Platelet aggregation and the inactivation of cell-free and cell-associated VSV and M13 were assayed and reported as described in Example 1. The results (Table II) indicate that with 30 minutes of UVA irradiation, the presence of type II quenchers decreased the inactivation of cell-free VSV by AMT, and this suppression of kill increased with increased concentration of the type II quencher. Since platelet function was not protected by type II quencher inclusion, effective virus kill with AMT and UVA in platelet concentrates appeared to be decreased with the addition of type II quenchers.

Table II also indicates that while the inactivation of the lipid enveloped virus VSV was inhibited, kill of the non-enveloped bacteriophage M13 was unchanged by the inclusion of type II quenchers.

TABLE II

Addition of Type II Quenchers: Effects on Platelet Aggregation and Virus Kill.

| Quencher (Con. [mM]) | Aggregation Response % control | | | Virus Kill $(\log_{10})^{(3)}$ | | |
|---|---|---|---|---|---|---|
| | $30^{(1)}$ | 60 | 90 | Cell-free VSV | Cell-assoc. VSV | M13 |
| α-tocopherol phosphate (.5) | 76 | 55 | 35 | 4.8 | | |
| α-tocopherol phosphate (1.0) | 75 | 60 | 40 | 4.0 | $.5, 1.5^{(4)}, 2^{(5)}$ | $1, 2^{(4)}, 3^{(5)}$ |
| α-tocopherol phosphate (2.0) | 70 | 50 | 30 | 3.5 | | |
| Tryptophan (2) | 70 | 50 | 30 | 5.5 | 1 | 1 |
| Tryptophan (4) | 60 | 45 | 20 | 4.9 | | |
| Tryptophan (10) | 45 | 20 | 0 | 4.0 | .5 | 1 |
| Histidine (5) | 75 | 55 | 35 | 5.1 | | |
| Histidine (10) | 65 | n.a$^{(2)}$ | n.a$^{(2)}$ | 4.8 | | |
| none (—) | 75 | 52 | 35 | $\geq 6.0$ | $1, 2^{(4)}, 3^{(5)}$ | $1, 2^{(4)}, 3^{(5)}$ |

$^{(1)}$minutes UVA exposure;
$^{(2)}$n.a = not available;
$^{(3)}$unless otherwise indicated kill results only with 30 minutes of UVA are provided;
$^{(4)}$kill results with 60 minutes UVA;
$^{(5)}$kill results with 90 minute UVA.

Figure 1C:
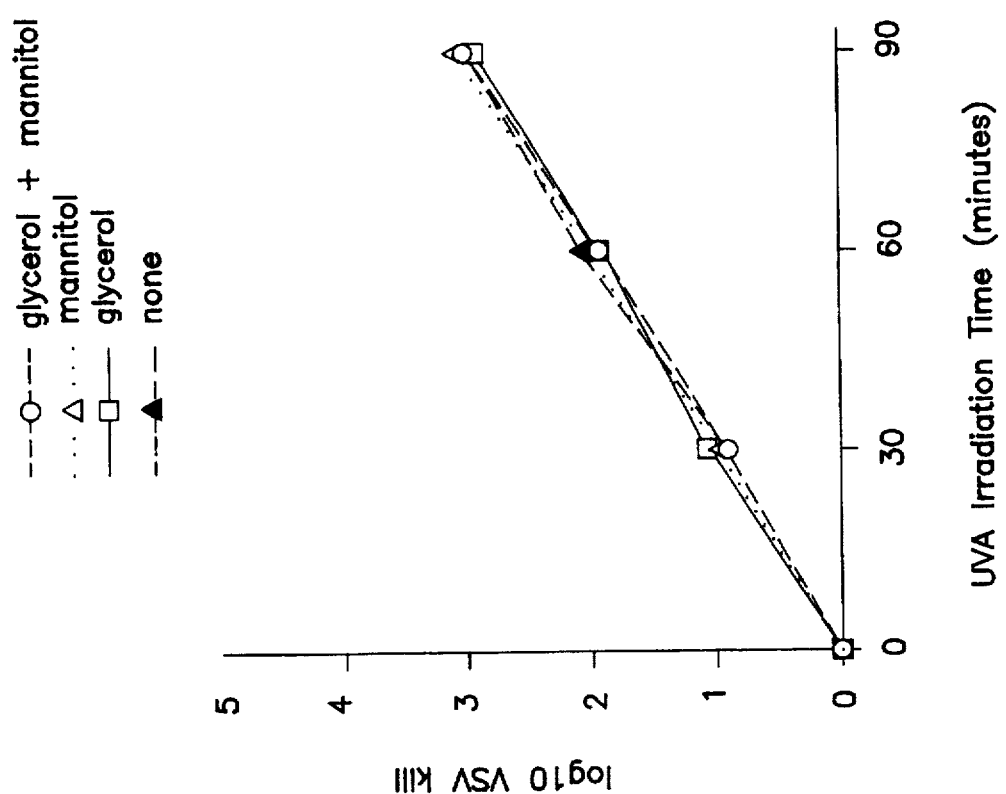
FIG. 1c depicts the virus kill results for cell-associated VSV.

Example 3. Effect of inclusion of mixtures of type I quenchers during treatment of a platelet concentrate with AMT and UVA Platelet concentrate aliquots (3 ml) were treated with 25 µg/ml AMT and 11 mW/cm² UVA for the times indicated in the absence or individual presence of the type I quenchers mannitol (2 mM) or glycerol (4 mM), or in the presence of the mixture of these two type I quenchers. Results (FIG. 1) are shown for platelet function (FIG. 1a) and for the inactivation of cell-free (FIG. 1b) and cell-associated (FIG. 1c) VSV and M13 (FIG. 1d), which were assayed as described in Example 1.

The effects of addition of the mixture of the type I quenchers mannitol and glycerol on platelet function (FIG. 1a) and virus kill (FIGS. 1b, 1c, 1d) are similar to the effects of addition of individual type I quenchers as described in Example 1. Virus kill is equivalent in the absence or presence of mixtures of type I quenchers, and platelet function after the 30 minute UVA treatment which yields complete kill of cell-free VSV, is improved by type I quencher presence. However, with the treatment times of 60 minutes or more which are necessary for more than 1 $\log_{10}$ kill of cell-associated virus or of M13, platelet function is compromised whether or not type I quenchers are included, alone or in combination.

Other type I quencher mixtures, e.g., 2 mM mannitol or 4 mM glycerol combined with 2 mM glutathione (not shown), gave equivalent results to those obtained with the combination of mannitol and glycerol, and provided no more protection to platelets than either of the type I quenchers that made up the mixture.

Example 4. Effect of inclusion of mixtures of type II quenchers during treatment of a platelet concentrate with AMT and UVA A platelet concentrate (3 ml aliquots) was treated with 25 µg/ml AMT and 11 mW/cm² UVA for 30, 60 or 90 minutes in the presence or absence of the mixture of the type II quenchers α-tocopherol phosphate (1 mM) and tryptophan (5 mM), or in the individual presence of either quencher. Results (FIG. 2) for platelet function (FIG. 2a) and virus kill of cell-free VSV (FIG. 2b), were assayed and reported as described in Example 1.

The inclusion of type II quenchers, either individually or combined with other type II quenchers, did not provide protection to platelets (FIG. 2a). In addition, the presence of type II quenchers decreased the rate of kill of cell-free VSV by AMT and UVA in air, and this suppression of kill was additive with combined type II quenchers. In 30 minutes kill was complete ($\geq 6.0 \log_{10}$) with no quenchers present, while in the individual presence of 1 mM α-tocopherol or 5 mM tryptophan kill was only about 4.2 $\log_{10}$, and with the combined presence of these quenchers kill was further reduced to about 2.8 $\log_{10}$ (FIG. 2b). Other mixtures of type II quenchers, e.g., tryptophan or α-tocopherol in combination with 5 mM histidine (not shown), had similar effects; they did not protect platelet function and their combined inclusion caused a decrease in the rate of kill of cell-free VSV which was more than that of either of the individual quenchers. Thus, platelet function was compromised under all conditions of AMT and UVA treatment in the presence of type II quenchers (alone or in combination) in which $\geq 6$ $\log_{10}$ of cell-free VSV were inactivated.

Figure 3B:
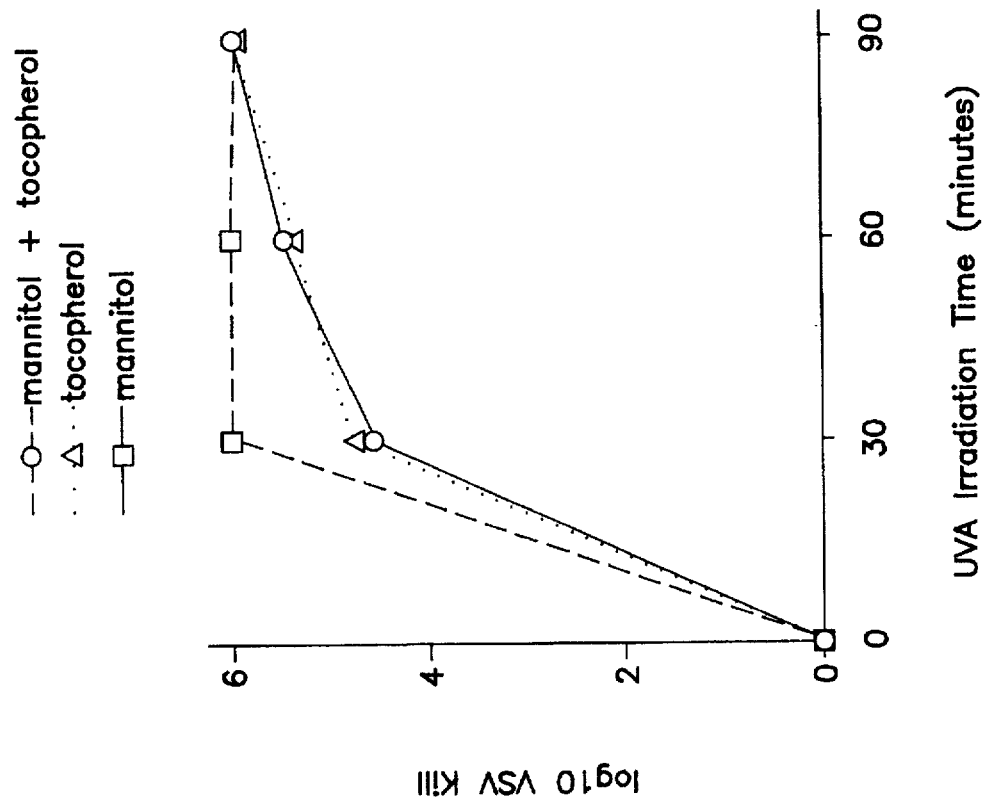
FIG. 3b depicts the virus kill results for inactivation of cell-free VSV.
Figure 3A:
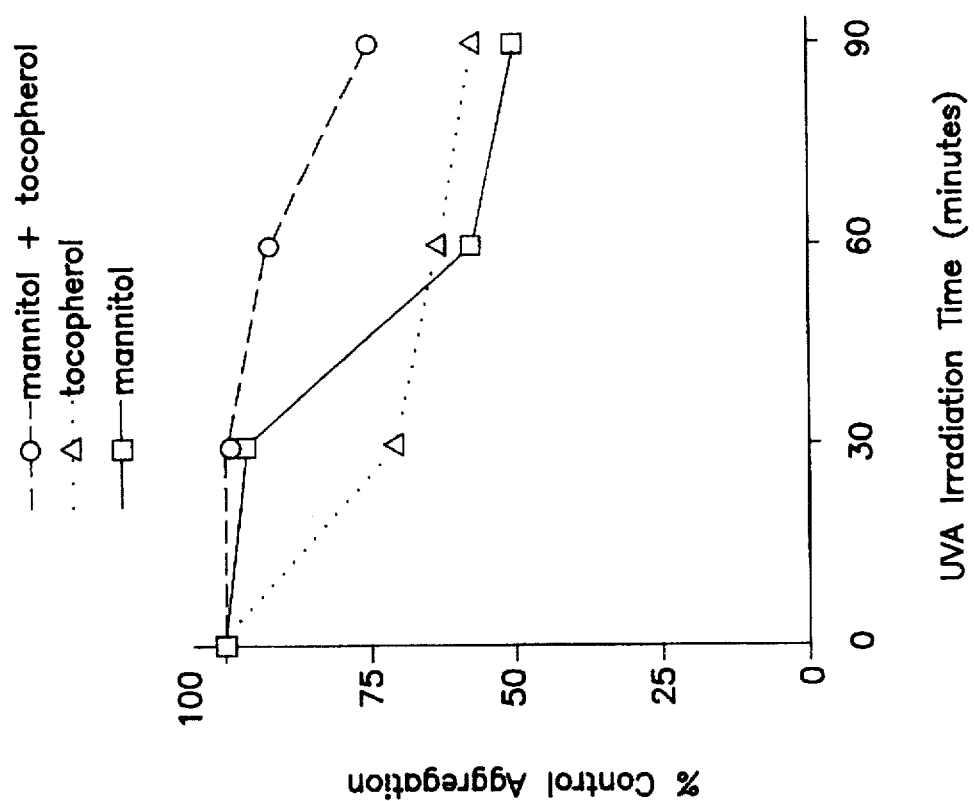
FIG. 3a depicts the results for platelet function.
Figure 3D:
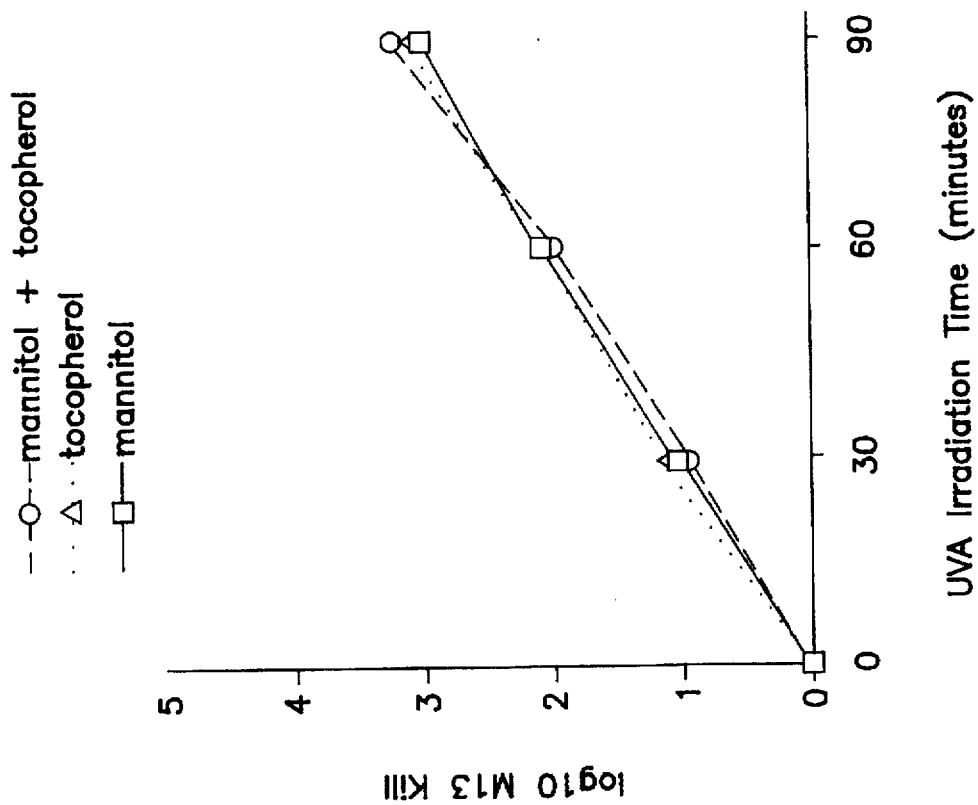
FIG. 3d depicts the virus kill results for bacteriophage M13.
Figure 3C:
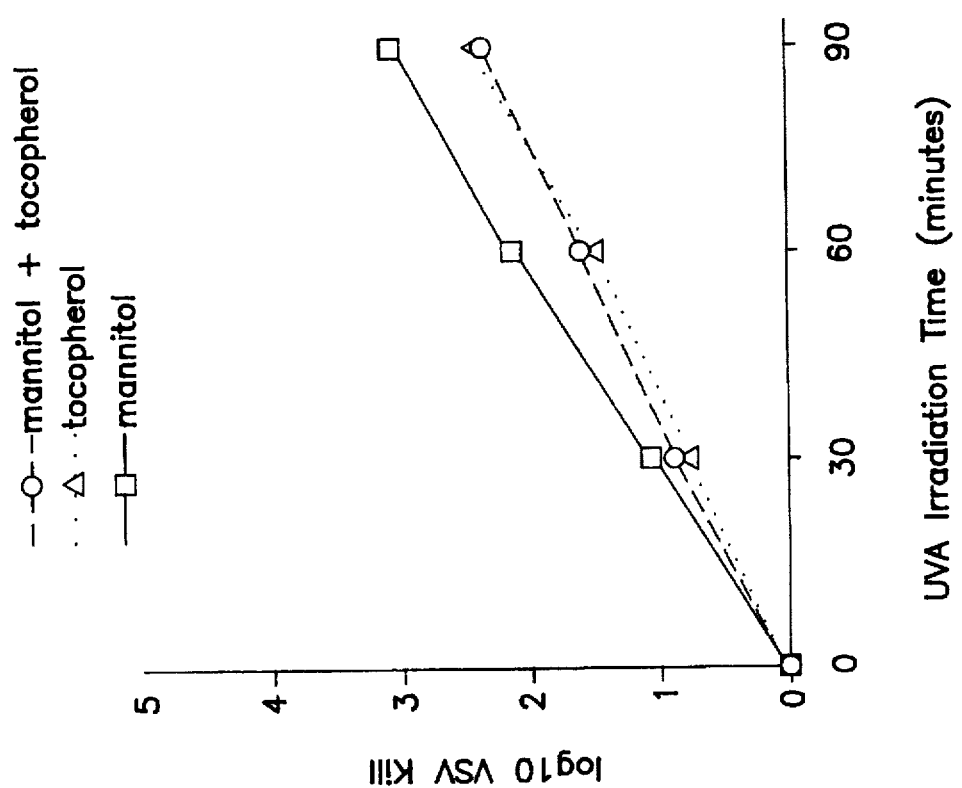
FIG. 3c depicts the virus kill results for cell-associated VSV.

Example 5. Effect of inclusion of mixtures of type I and type II quenchers during treatment of a platelet concentrate with AMT and UVA Platelet concentrate aliquots (3 ml) were treated with 25 µg/ml AMT and 11 mW/cm² UVA for 30, 60 or 90 minutes in the presence of a mixture of the type I quencher mannitol (2 mM) and the type II quencher α-tocopherol phosphate (1 mM), or in the individual presence of mannitol or α-tocopherol. Platelet function (FIG. 3a) and virus kill (FIGS. 3b, 3c, 3d) were assayed and reported as in Example 1.

With 30 minutes of irradiation, platelet function (FIG. 3a) was preserved with either the addition of the individual type I (mannitol) quencher or with the combination of mannitol (type I) and α-tocopherol phosphate (type II). With 60 minutes or longer of UVA, the combined presence of mannitol and α-tocopherol phosphate improved platelet aggregation (from about 70% to more than 90% of the control with 60 minutes of UVA), whereas the individual presence of each of these quenchers did not. Functional results using glycerol as the type I quencher were similar to those for mannitol combined with α-tocopherol. With all type I plus type II combinations tested, virus kill results with combined quenchers were the same as those for the type II quencher alone, and the rate of kill of cell-free (FIG. 3b) and cell-associated (FIG. 3c) VSV were somewhat decreased while that of M13 (FIG. 3d) was unaffected by type II quencher addition.

With the longer irradiation times made possible by the addition of the combination of the type I and type II quenchers, mannitol (or glycerol) and α-tocopherol, the effective range of virus kill by AMT and UVA in platelet concentrates was increased.

Figure 4B:
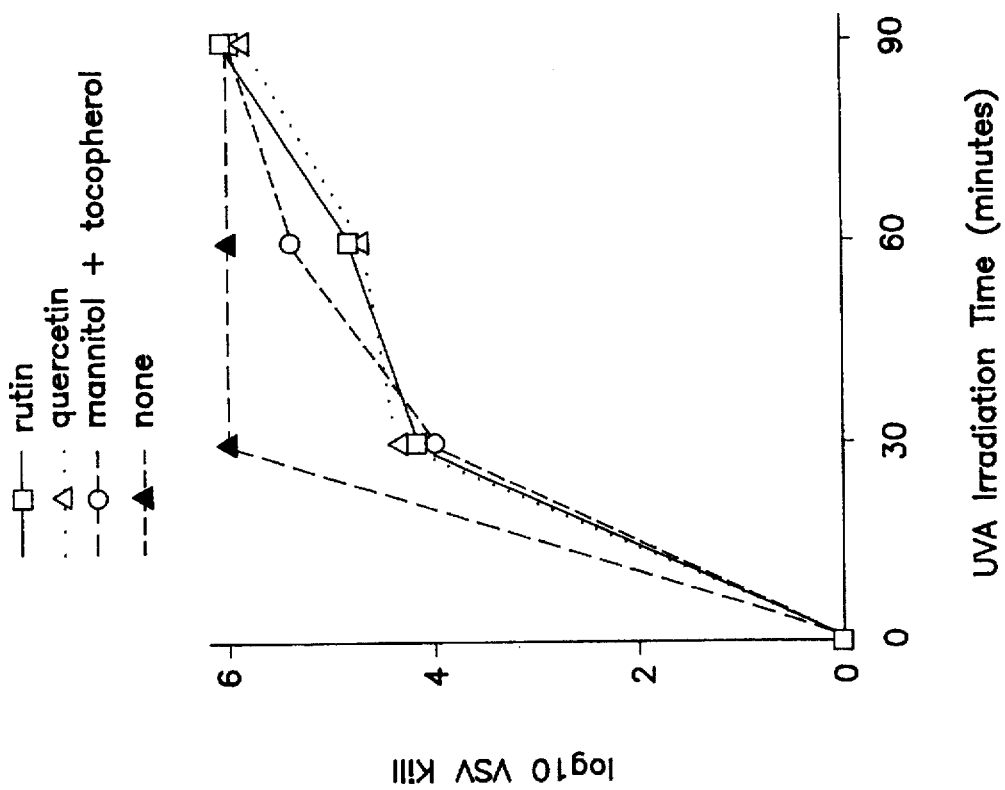
FIG. 4b depicts the virus kill results for VSV.
Figure 4A:
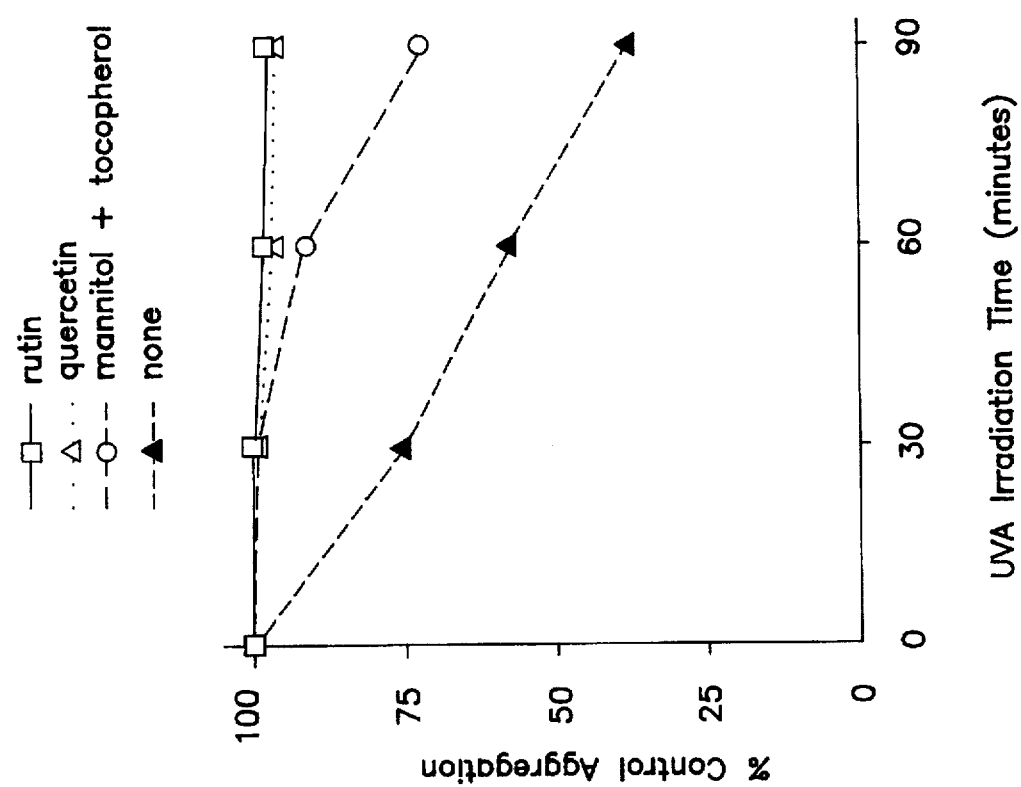
FIG. 4a depicts the results for platelet function.

Example 6. Effect of inclusion of compounds which quench both type I and type II photodynamic reactions during treatment of a platelet concentrate with AMT and UVA Platelet concentrate aliquots (3 ml) were treated with 25 µg/ml AMT and UVA (11 mW/cm²) for 30, 60, or 90 minutes in the absence or presence of 0.25 mM quercetin or 0.25 mM rutin, or with the mixture of 1 mM α-tocopherol phosphate and 2 mM mannitol. Platelet function and virus inactivation were assayed and reported as in Example 1 (FIG. 4).

The effects of inclusion of the flavonoids quercetin or rutin, compounds known to efficiently quench both type I and type II photodynamic reactions, were similar to those obtained when mixtures of type I and type II quenchers were included during treatment. The rate of kill of VSV (FIG. 4b), but not that of M13 (not shown, see FIG. 3d), decreased, and platelet function (FIG. 4a) was protected, even with the longer irradiation times required for complete kill of cell-free VSV.

Example 7. Flavonoid effects on platelet aggregation

Collagen induced aggregation is a sensitive indicator of platelet function and results with collagen usually correlate well with those for platelet morphology, activation and thromboxane and ATP release, as well as aggregation induced by other agonists. The aggregation response (extent and initial rate of aggregation as compared to the untreated control) to collagen following treatment with 25 µg/ml AMT and 90 minutes UVA are provided (Table III). Table III indicates that each of the flavonoids tested protected the collagen induced aggregation response.

TABLE III

Effects of flavonoid addition on the platelet aggregation response following treatment with AMT and UVA.

| Flavonoid Quencher | Glycon Form | % Untreated Control- Extent/Rate of Aggregation Response to Collagen[1] | |
|---|---|---|---|
| | | untreated | treated |
| none | — | 100/100 | 44/24 |
| quercetin | — | 100/100 | 98/98 |
| chrysin | — | 100/100 | 90/85 |
| rutin | + | 100/100 | 100/100 |
| hesperidin | + | 98/90 | 100/86 |
| naringin | + | 90/83 | 78/61 |

[1]prior to overnight storage, sample was treated with 25 µg/ml AMT and 90 minutes of UVA in the absence or presence of flavonoid indicated.

Example 8. Effect of inclusion of compounds which quench both type I and type II photodynamic reactions during treatment of a platelet concentrate with UVA and increasing concentrations of AMT Because only 3 $\log_{10}$ of cell-associated VSV were inactivated using an AMT concentration of 25 µg/ml, the effects of higher concentrations of AMT were assessed with and without the addition of various quenchers. Platelet concentrate aliquots (3 ml) were treated with UVA (11 mW/cm²) for 90 minutes in the presence of AMT at concentrations of 25, 50 or 100 µg/ml, with out without the addition of 0.7 mM rutin, 0.7 mM quercetin or 2 mM mannitol. Platelet aggregation in response to collagen (FIG. 5a) and the inactivation of cell-associated VSV (FIG. 5b) were assayed and reported as described in Example 1.

Figure 5B:
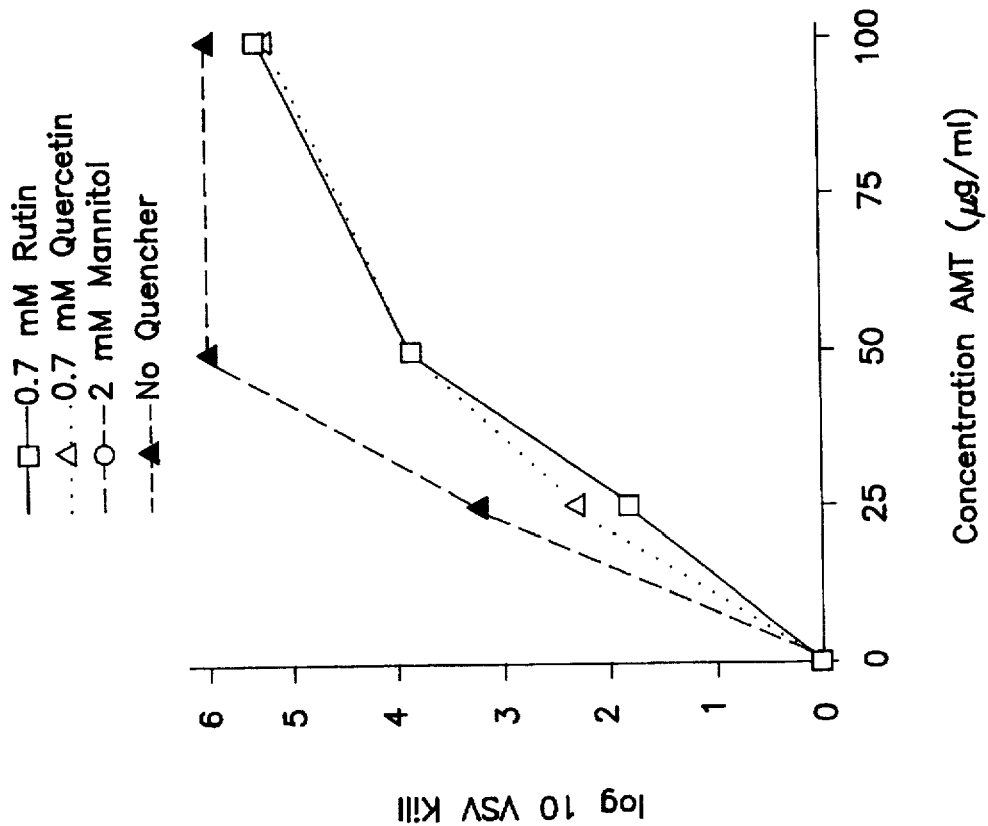
FIG. 5b depicts the virus kill results for VSV.
Figure 5A:
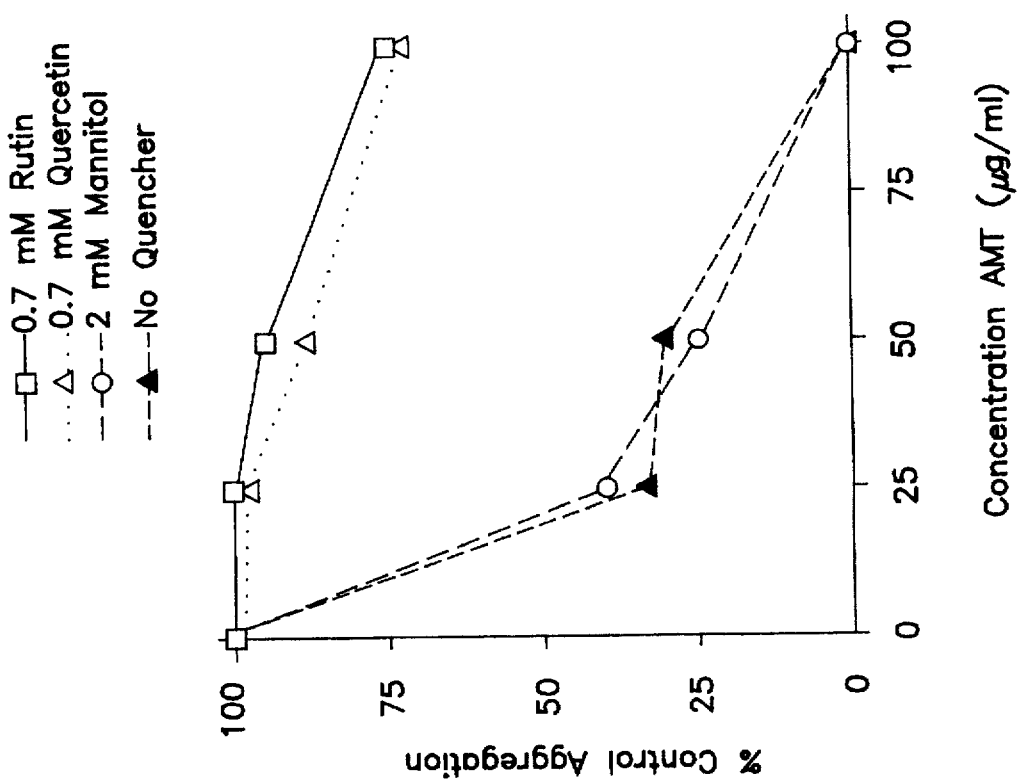
FIG. 5a depicts the results for platelet function.

On treatment of platelets with 90 minutes of UVA and 25 µg/ml AMT the aggregation response to collagen was only about 35% of the control and, as noted above, the addition of mannitol did not protect platelet function with this irradiation treatment. Aggregation was further decreased (to less than 30% with 50 µg/ml and to no response at all with 100 µg/ml AMT) with increasing AMT concentration whether or not mannitol was present. When 0.7 mM rutin was included during treatment, aggregation function was increased to more than 80% of the control with all of the AMT concentrations tested (FIG. 5a). Cell-free VSV (not shown) was completely inactivated under all these treatment conditions, and with 100 µg/ml AMT and 0.7 mM rutin (or quercetin) present the inactivation of cell-associated VSV was almost 6 $\log_{10}$ (FIG. 5b). Thus, by the inclusion of compounds which quench both type I and type II photodynamic reactions (e.g., flavonoids such as rutin), during treatment of a platelet concentrate with psoralens and UVA, platelet aggregation function was well maintained under conditions where almost 6 $\log_{10}$ cell-associated virus were inactivated in the presence of oxygen.

Example 9: Effects of deoxygenation as compared to rutin addition during treatment of a platelet concentrate with AMT and UVA Platelet concentrate aliquots were treated with AMT at the concentration indicated and 90 minutes of UVA, either in air in the absence or presence of rutin, or with the air in the tube exchanged with a combination of nitrogen (95%) and $CO_2$ (5%). Platelet aggregation was assessed as in Example 1 after overnight storage in air. Table IV shows that with an AMT concentration of 50 μg/ml, although both deoxygenation and rutin addition were capable of improving platelet function following AMT/UVA treatment, results with rutin were consistent from experiment to experiment, while those with gas exchange were more variable and frequently showed no benefit at all.

TABLE IV

Platelet aggregation following 90 minute AMT and UVA treatment. Effect of rutin vs. oxygen removal on consistency of results.

| Expt. | AMT concentration | air no quencher | air +0.5 mM Rutin | deoxygenated no quencher |
|---|---|---|---|---|
| 1 | 50 μg/ml | 32/33 | 100/100 | 95/100 |
| 2 | 50 μg/ml | 42/31 | 98/95 | 90/85 |
| 3 | 50 μg/ml | 36/18 | 95/90 | 56/36 |
| 4 | 50 μg/ml | 70/30 | 96/96 | 91/94 |
| 5 | 50 μg/ml | 21/13 | 100/84 | 3/13 |

Figure 6:
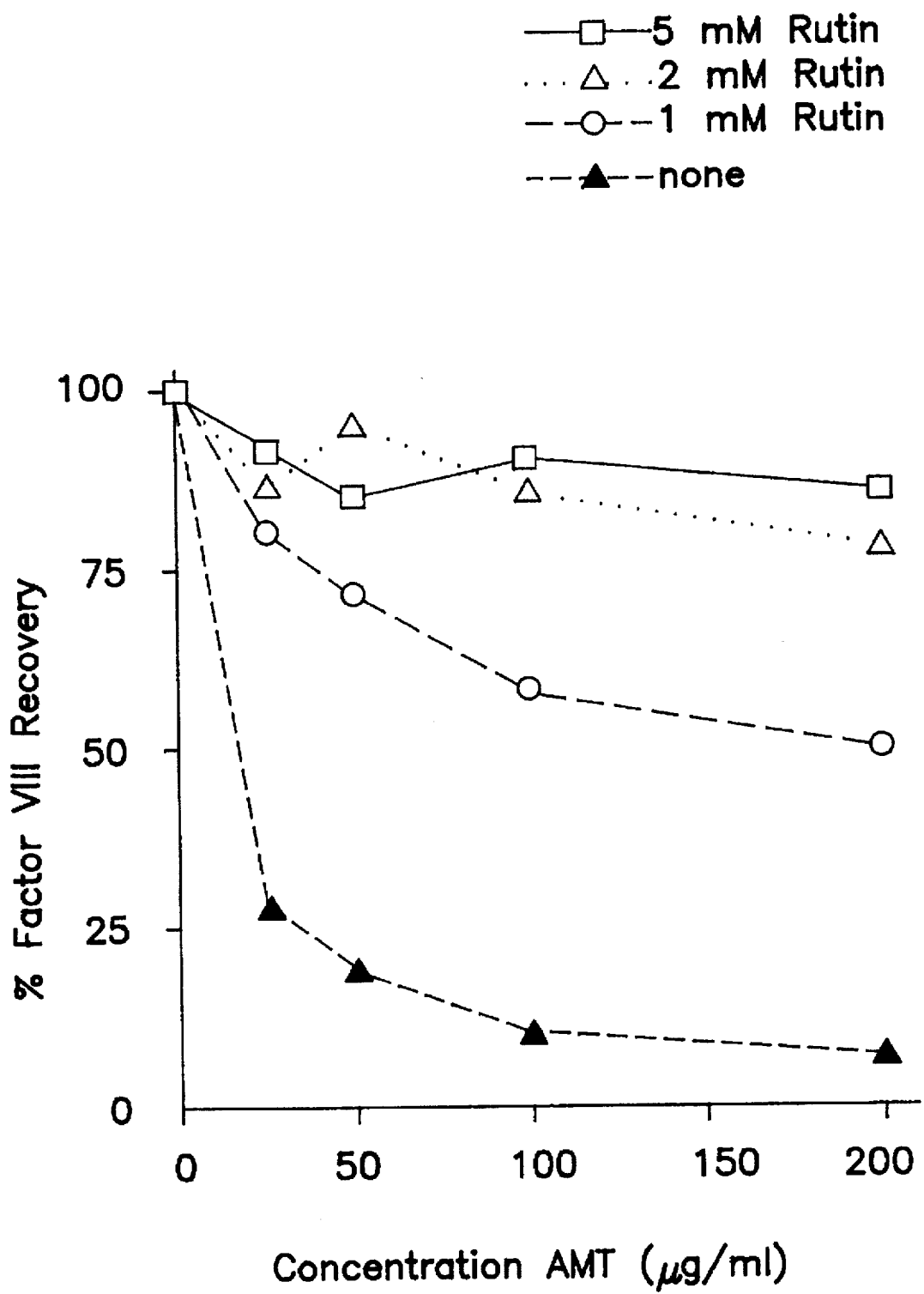
FIG. 6 comprises one graph depicting the effect on the recovery of coagulation factor VIII of the inclusion of rutin during the viral inactivation treatment of plasma by AMT and UVA.

Example 10. Improved recovery of coagulation factors on treatment of plasma with AMT and UVA with the inclusion of compounds which quench both type I and type II photodynamic reactions Human plasma (3 ml aliquots) was treated with 25, 50, 100 or 200 μg/ml of AMT and irradiation with UVA (11 mW/cm$^2$) for 90 minutes. Recovery of coagulation factor VIII (Antihemophilic Factor, AHF) in samples treated with or without the inclusion of 1, 2 or 5 mM rutin was compared. The results are shown in FIG. 6. On treatment of plasma with 25 μg/ml AMT and 90 minutes of UVA, AHF recovery in the absence of rutin was only 27% of the untreated control and this low value decreased further with increased psoralen concentration, and with 200 μg/ml AMT treatment, recovery was only 7%. Remarkably, AHF recovery was restored to 83% or greater when rutin was included during treatment (at concentrations of 2 mM or greater for AMT concentrations of up to 100 μg/ml, or at 5 mM with an AMT concentration of 200 μg/ml, and with ≧25 μg/ml of AMT, these treatment conditions were sufficient to inactivate at least 4 log 10 of the non-enveloped bacteriophage M13.

Thus, by the addition of rutin, a compound known to quench both type I and type II photodynamic reactions, during treatment of plasma with psoralens and UVA, a significant increase in coagulation factor VIII recovery can be obtained with oxygen present, under conditions where non-enveloped virus can be inactivated.

The next set of examples, which are set forth below, make reference to "solvent-detergent" and/or "SD" treatment. In each case, the protocol for this treatment was as follows: AHF concentrates were treated with 0.3% tri(n-butyl) phosphate (TNBP) and 1% Tween 80 for 6 hours at 24° C. after which the added reagents were removed, where indicated, by ion exchange chromatography. Plasma was treated with 1% TNBP and 1% Triton X-100 for 4 hours at 30° C., after which the added reagents were removed by hydrophobic chromatography on a C18-containing resin.

Example 11: UV treatment of AHF concentrate in the absence of added quenchers

Figure 7:
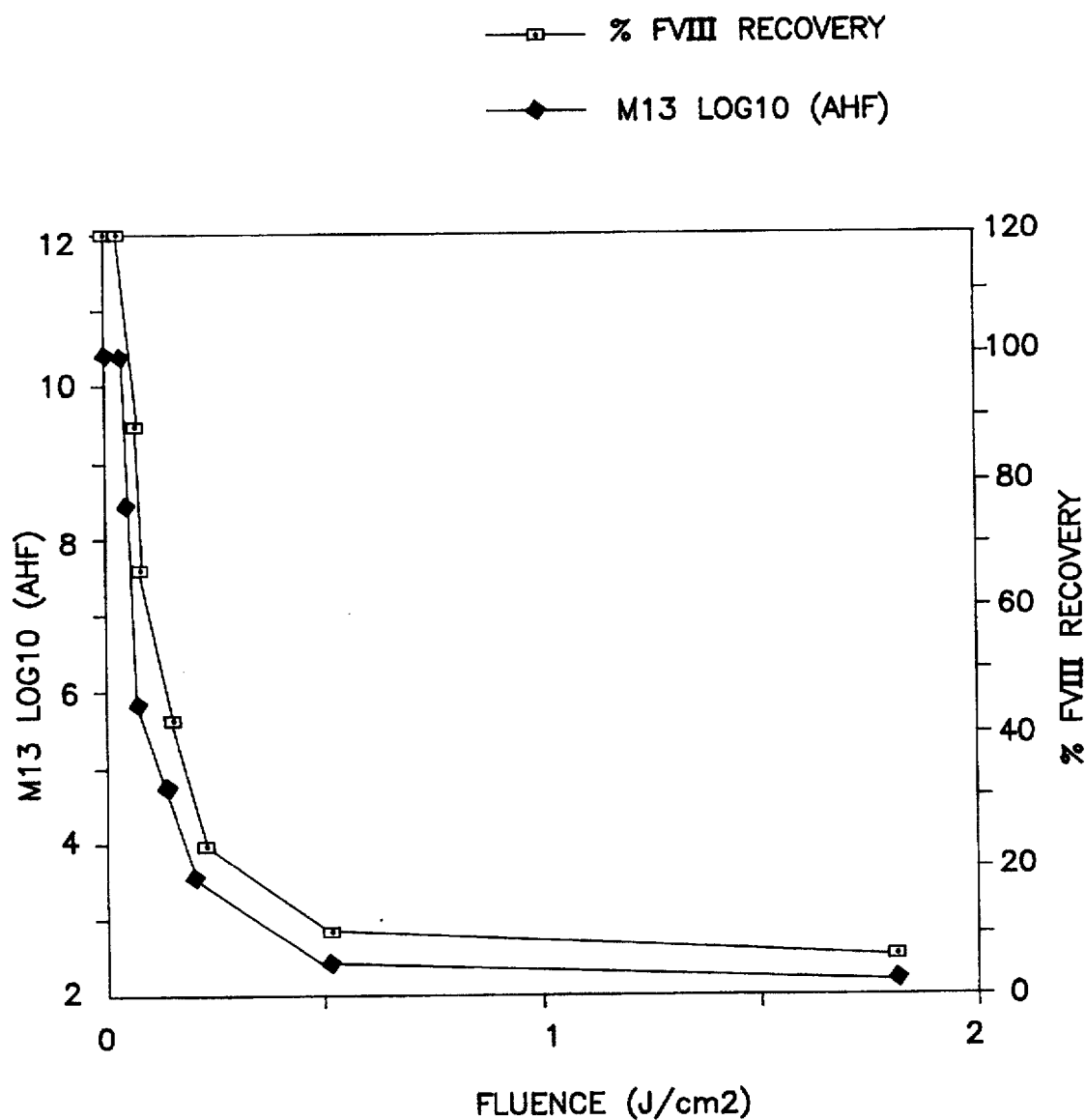
FIG. 7 comprises a single graph depicting the influence of UVC treatment of AHF concentrate with respect to bacteriophage M13 infectivity and FVIII recovery.

Phage M13, a non-enveloped virus, was added to an AHF concentrate. The mixture was subjected to a varying dose of UV irradiation in a quartz flow cell by varying flow rate. The source of UV light was a BLEIT155 bulb (Spectronic Co., Westbury, N.Y.). Before and after irradiation, Phage M13 infectivity was measured by plaque assay on host JM101 cells; AHF activity was measured in a clot assay. The results, shown in FIG. 7, indicate that under conditions where a 5 $\log_{10}$ inactivation of Phage M13 was achieved, factor VIII recovery was less than 50%.

Example 12: UV treatment of plasma in the presence of quercetin and ascorbate

The non-enveloped Phage M13 was added to plasma. Treatment of the mixture in the presence of 0.75 mM ascorbate and 0.20 mM quercetin (final concentration) with 0.073 J/cm$^2$ to 0.134/cm$^2$ UV resulted in the inactivation of 6.2 to 6.5 $\log_{10}$ (ID$_{50}$) of M13, while FVIII & FIX recovery were 82–97% and 81–94%, as shown in Table V below:

TABLE V

| UV Dosage (J/cm$^2$) | Phage Kill ($\log_{10}$) | | FVIII Recovery % | | FIX Recovery | |
|---|---|---|---|---|---|---|
| | −Quencher | +Quencher | −Quencher | +Quencher | −Quencher | +Quencher |
| 0 | | 0 | 100 | 100 | 100 | 100 |
| 0.073 | 5.5 | 6.4 | 63 | 86 | 65.5 | 81.0 |
| 0.083 | 5.6 | 6.5 | 62 | 82 | 60.0 | 83.0 |
| 0.099 | 6.7 | 6.5 | 64.8 | 83 | 60 | 94.0 |
| 0.134 | 5.3 | 5.5 | 73 | 97 | 59.6 | 85.0 |

Note that factor VIII and factor IX recovery in the presence of quenchers is significantly higher, while quencher addition had no significant effect on virus kill.

Example 13: UV treatment of AHF concentrate in the presence of quercetin and ascorbate AHF prior to the solvent-detergent inactivation step in the manufacture process was treated with UV at 0.086 J/cm$^2$, after adding EMC or VSV. Other conditions were the same as described in example 12. It is shown in Table VI below that ≧7.0 $\log_{10}$ EMC and VSV were inactivated. Corresponding recovery of FVIII was 80.0% when quenchers were present during irradiation. This compared with 33% without quenchers.

TABLE VI

| | Virus Kill log$_{10}$ | | | | FVIII Yield % | |
| | −Quencher | | +Quencher | | | |
| UV Dosage | EMC | VSV | EMC | VSV | −Quencher | +Quencher |
|---|---|---|---|---|---|---|
| 0 | 0 | 0 | 0 | 0 | 100 | 100 |
| 0.086 | ≧7.0 | ≧7.0 | ≧7.0 | ≧7.0 | 33 | 80 |

Example 14: Combined Treatment of Plasma with UV and SD

Virus was added to solvent-detergent treated plasma and treated with UV at 0.083 J/cm². Table VII shows that EMC kill was ≧7.7, VSV ≧6.5 and AAV ≧3.0, while coagulation factor recovery was generally 79–105% and fibrinogen yield was 107 to 113% when quenchers were present. These values are 30–50% better than when quenchers were not added. Again, under these conditions virus kill was unaffected.

TABLE VII

| UV Dosage | +Quencher [Ascorbate Quercetin or Rutin] | Virus Kill (log$_{10}$) | | | Fibrinogen & Coagulation Factory Recovery (%) | | | | | |
|---|---|---|---|---|---|---|---|---|---|---|
| | | EMC | AAV | VSV | FV | FVII | FVIII | FIX | FXI | FRN |
| 0 | − | 0 | 0 | 0 | 100 | 100 | 100 | 100 | 100 | 100 |
| 0 | + | 0 | 0 | 0 | 100 | 103 | 100 | 93.9 | 112.5 | 106–114 |
| 0.083 | − | ≧7.7 | ≧3.0 | ≧6.5 | 54 | 46–54 | 58 | 40 | 70 | 76 |
| 0.083 | + | ≧7.7 | ≧3.0 | ≧6.5 | 83–93 | 70–87 | 88–100 | 79–94 | 86–105 | 107–113 |

Example 15: Combined Treatment of AHF Concentrate with UV and SD

Solvent-detergent-treated Factor VIII concentrate, rehydrated in 10.0 ml water per vial was spiked with polio virus type 2, which is a non-lipid-enveloped small marker virus. Treatment with UV at 0.083 J/cm², resulted in ≧5.0 log$_{10}$ inactivation. FVIII yield was 81–94%. The corresponding values in the absence of quencher were 30–40% lower. In another example in which AHF concentrate spiked with HAV (Hepatitis A Virus) was treated, HAV kill was ≧4 logs while FVIII recovery was similar to above. The results are summarized in Table VIII.

TABLE VIII

| UV Dosage J/cm² | Quencher and Quencher Concentration | Polio Virus Kill (log$_{10}$) | FVIII Recovery (%) | HAV Kill log$_{10}$ |
|---|---|---|---|---|
| 0 | −Quenchers | 0 | 100 | 0 |
| 0 | +Quenchers | 0 | 100 | 0 |
| 0.083 | +0.75 mM Ascorbate +0.2 mM Quercetin | ≧5.6 | 80.8 | ≧4.4 |
| 0.083 | +0.75 mM Ascorbate +0.5 mM Rutin | ≧5.3 | 93.9 | ≧4.4 |

Example 16: Treatment of Plasma with UVC in the Presence of Varying Quenchers

Plasma was treated with UV at 0.064 to 0.09 J/cm² in the presence of various quenchers. Table IX shows the recovery of various factors and fibrinogen under the conditions of treatment. Based on the above, the retention of coagulation factors and fibrinogen activity is best when UV treatment occurs in the presence of the flavinoids with or without added ascorbate or histidine. It is significant to note that the presence of these quenchers did not compromise kill of any of the marker viruses tested.

TABLE IX

| Quencher | Virus Kill (log$_{10}$) | | | Coagulation Factor Recovery (%) | | | | | |
|---|---|---|---|---|---|---|---|---|---|
| | M13 | EMC | VSV | FV | FVII | FVIII | FIX | FXI | FBN |
| FLAVO-NOIDS | | | | | | | | | |
| None | 5.5 | ≧7.7 | ≧6.5 | 59 | 67 | 54 | 50 | 49 | 75 |
| Quercetin | 5.0 | ≧7.7 | ≧6.5 | 75 | 97 | 70 | 46 | 50 | 82 |
| Rutin | — | ≧7.7 | ≧5.4 | 75 | 104 | 86 | 63 | 63 | 96 |
| FLAVONOID MIXTURES | | | | | | | | | |
| Quercetin + Ascorbate | — | ≧7.7 | ≧6.5 | 72 | 100 | 93 | 97 | 107 | 91 |

TABLE IX-continued

| Quencher | Virus Kill (log$_{10}$) | | | Coagulation Factor Recovery (%) | | | | | |
|---|---|---|---|---|---|---|---|---|---|
| | M13 | EMC | VSV | FV | FVII | FVIII | FIX | FXI | FBN |
| Chrysin + Ascorbate | — | ≧6.5 | ≧6.5 | 92 | 101 | 86 | 100 | 113 | 96 |
| Quercetin + Histidine | — | ≧6.0 | ≧6.5 | — | — | 105 | 136 | — | — |
| TYPE I or TYPE II QUENCHERS ALONE | | | | | | | | | |
| Ascorbate | 4.7 | ≧7.7 | ≧6.5 | 67 | 97 | 73 | 54 | 52 | 86 |
| Histidine | 4.0 | — | — | — | — | 79 | 69 | — | — |
| Glutathione | 4.4 | — | — | — | — | 78 | 68 | — | — |
| Tryptophan | 4.0 | — | — | — | — | 79 | 69 | — | — |
| Mannitol | 6.6 | — | — | — | — | 60 | 58 | — | — |
| Glycerol | 6.6 | — | — | — | — | 49 | 51 | — | — |
| Superoxide dismutase | 3.9 | — | — | — | — | 84 | 82 | — | — |
| SCNAT | 1.6 | — | — | — | — | 75 | 81 | — | — |

Example 17: Recovery of FVIII in UV treated plasma with varying concentration of Quenchers (Ascorbate and Quercetin)

Figure 8B:
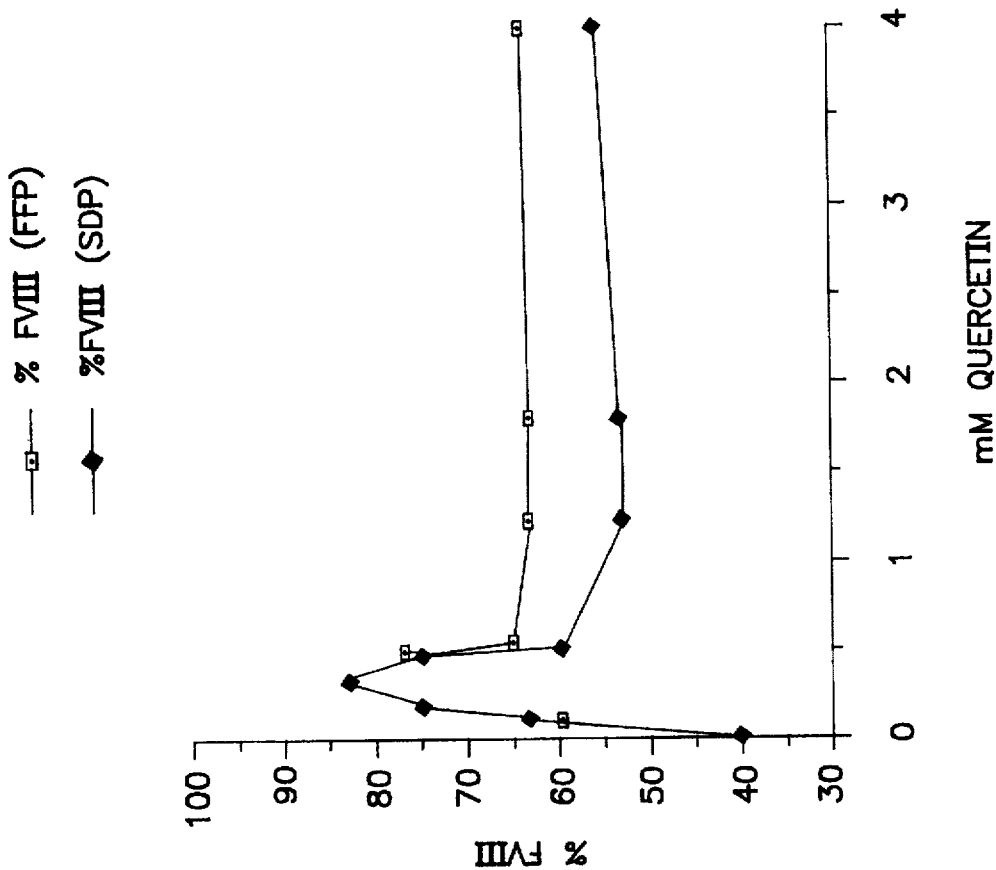
FIG. 8 comprises two graphs depicting the protective and optimal concentration of ascorbate in the presence of constant quercetin (FIG. 8a) and quercetin in the presence of constant ascorbate (FIG. 8b).
Figure 8A:
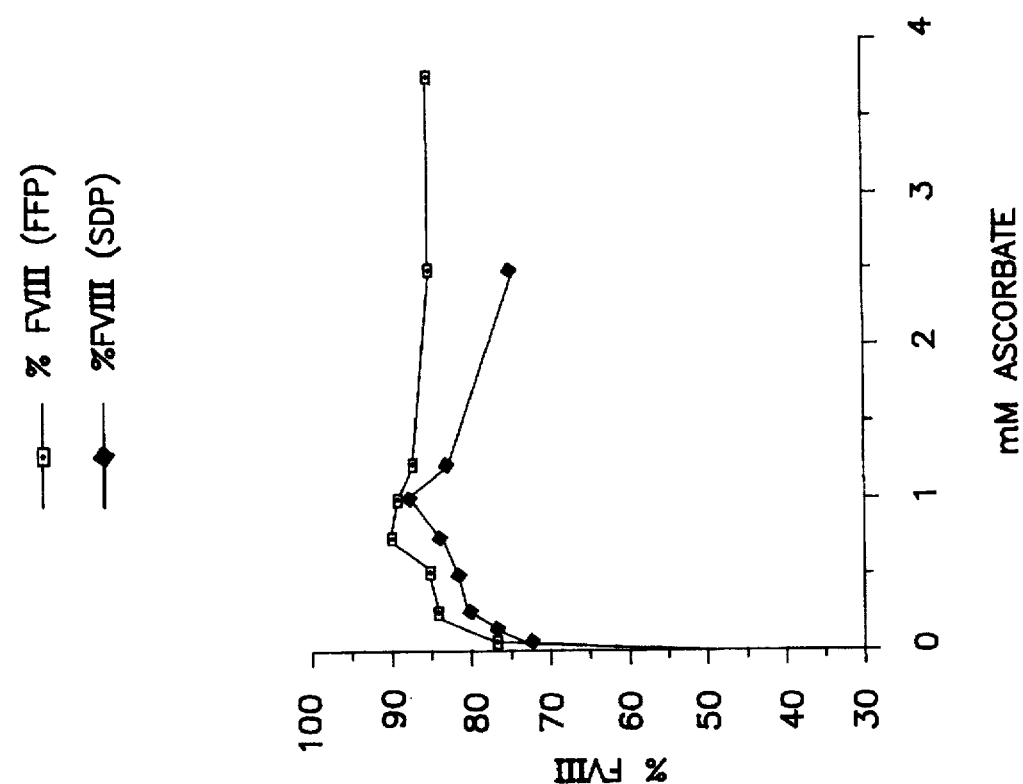

Solvent-detergent treated plasma was treated with UV at 0.0865 J/cm² in the presence of various concentrations of quercetin (0 to 1.75 mM) while keeping the final concentration of ascorbate in the plasma constant at 0.50 mM. Conversely, the final concentration of quercetin was kept constant at 0.20 mM while adding various concentrations of ascorbate (0 to 1.50 mM). The objective was to determine the best—optimal—levels of each of these compounds. The results, which are shown in FIGS. 8a and 8b, indicate that each of these stabilizers is self-limiting. Quercetin peaked at 0.20 mM. Ascorbate has a broader maximum, at 0.75 to 1.25 mM.

Example 18: Kinetics of virus (M13) kill in plasma and plasma derivative (solvent detergent treated AHF) at various dosages of UV (254 nM)

Figure 9A:
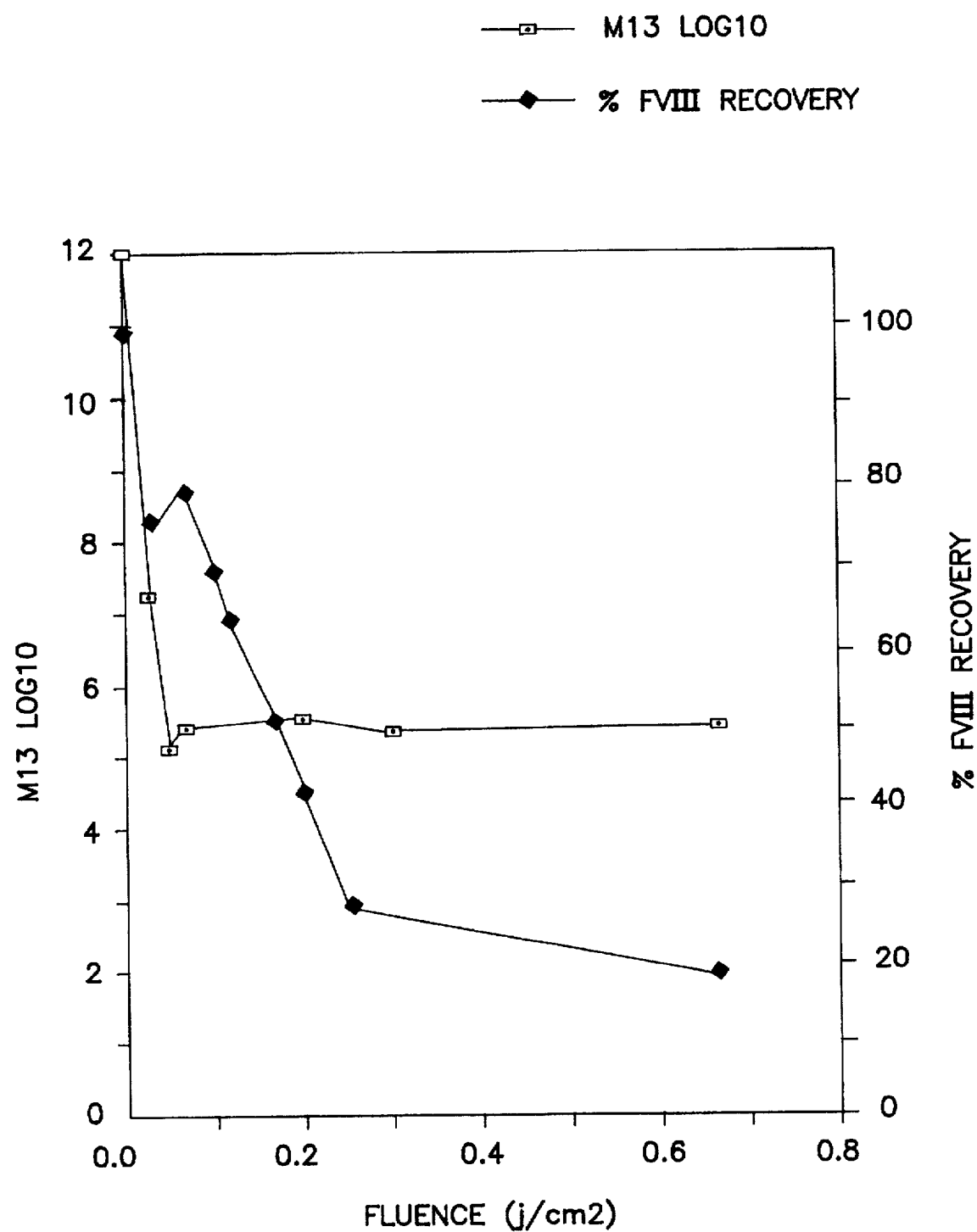
FIGS. 9A and 9B comprise graphs depicting the influence of UVC treatment in the presence of 0.5 mM ascorbate and 0.2 mM quercetin with respect to bacteriophage M13 infectivity and FVIII recovery.
Figure 9B:
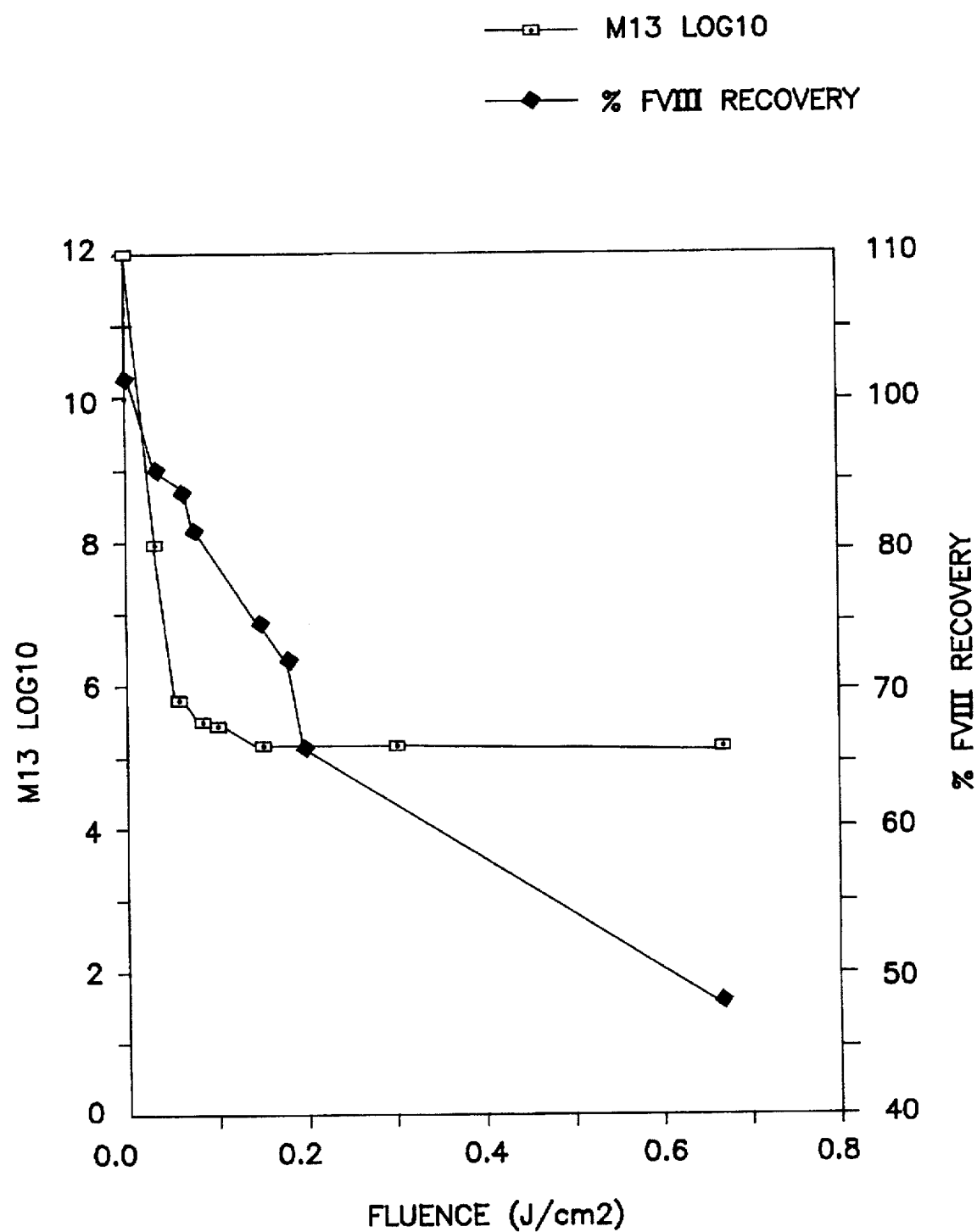

Fresh frozen plasma and solvent/detergent-treated AHF were independently seeded with the phage M13 and then treated at various UV doses, [0 to 0.6 J/cm$^2$] in the presence of quenchers (0.75 mM ascorbate and 0.2 mM quercetin). Flow rate varied with each UV dose. The results, shown in FIGS. 9a [AHF concentrate treated] and 9b [FFP treated], indicate that treatment @0.04 to 0.13 J/cm$^2$ where at least a 5 log$_{10}$ inactivation of phage M13 was achieved, factor VIII recovery was better than 80%.

Example 19: Treatment of a red cell concentrate with x-irradiation and a brominated sensitizer A red blood cell concentrate was treated with X-irradiation in the presence of a brominated hematoporphyrin derivative. The presence of 1 mm rutin reduced red cell hemolysis from 8% to less than 2%. Virus kill, as measured with M13, exceeded 5 log$_{10}$ in each case.

Example 20: Treatment of Plasma with Gamma-Irradiation

Fresh frozen plasma was treated with 40 kGy of gamma-irradiation. The recovery of coagulation factor IX was 77% in the absence of rutin and 90% in the presence of 2 mM rutin. The kill of VSV exceeded 5 log$_{10}$ in each case.

Example 21: Quencher enhanced photoinactivation of viruses

The following are additional examples supporting the conclusion that virus killing specificity in cell components and protein solutions by photoactive procedures can be enhanced with either a mixture of type I and type II quenchers or a bifunctional quencher:

Given what is known, virus kill is inferred as follows:

| PROJECTED VIRUS KILL IN S/D - UV COMBINED TREATMENT Virus Kill (log$_{10}$) | | | | | | |
|---|---|---|---|---|---|---|
| | EMC | Sindbis | VSV | AAV | HAV | Polio |
| S/D | 0 | ≧8.8 | ≧9.2 | 0 | 0 | 0 |
| UV | ≧7.7 | ≧8.7 | ≧6.5 | ≧3.0 | ≧4.4 | ≧5.6 |
| Combined | ≧7.7 | ≧17.5 | ≧15.7 | ≧3.0 | ≧4.4 | ≧5.6 |

Data given for (UV) treatment was obtained in the presence of 0.75 mM ascorbate and 0.20 mM Quercetin and fluence of 0.086 J/cm$^2$. Coagulation Factor Recovery was 80–90%.

Example 22. Lymphocyte Inactivation and Preservation of RBC and Platelet Integrity 1. Gamma-Irradiation a. τ-irradiation of RBCCs: RBCCs are treated with τ-irradiation at doses of 15, 25 or 50 Gy (1 Gy=1 Gray=100 Rads) using a cobalt-60 source in the presence or absence of 0.5, 1, or 2 mM rutin. Lymphocyte inactivation is determined by measurements of $^3$H thymidine uptake after mitogen (2% PHA final concentration) stimulation. Extracellular (plasma) potassium is measured after 7 days of storage at 4° C. and compared with unirradiated controls.

Irradiated lymphocytes retained only 1.5% of their $^3$H thymidine uptake after a 15 Gy exposure and none after 50 Gy and this was independent of the presence or concentration of quencher (rutin). Extracellular potassium increased with increasing irradiation dosage and was decreased to control levels by the presence of 2 mM rutin. With 50 Gy of τ-irradiation, lymphocytes were completely inactivated and plasma K+ was 80 mM in the absence of quenchers and 40 mM when 2 mM rutin was present during treatment. Thus, quenchers can be used to increase the specificity of gamma-irradiation of RBCCs for lymphocyte inactivation.

b. RBC samples treated first with AlPcS$_4$ and light, and then τ-irradiation in the presence of flavonoids: Following treatment of an RBCC (diluted with an equal volume of PBS) with 6.5 μM AlPcS$_4$ with 44 J/cm$^2$ visible light in the

| PRODUCT | INACTIVANT | QUENCHER | LOG$_{10}$ VIRUS KILL | | QUENCHER BENEFIT |
|---|---|---|---|---|---|
| | | | VSV | M13 | |
| Platelet Conc. | 50 μg/ml AMT + 57 J/cm$^2$ UVA | none 0.35 mM rutin | ≧6 ≧6 | 3 3 | agg response ↑ ≦3→85% |
| AHF Conc. | 0.1 J/cm$^2$ UVC | none 0.5 mM rutin + 0.75 mM asc | ≧7 ≧7 | 5.5 5.5 | AHF recovery ↑ 33→94% |
| FFP | 100 μg/ml AMT + 57 J/cm$^2$ UVA | none 2 mM rutin | ≧6 ≧6 | 5 5 | AHF recovery ↑ 11→83% |
| FFP | 0.1 J/cm$^2$ UVC | none 0.8 mM rutin | ≧6 ≧6 | 6 6 | AHF recovery ↑ 56→95% |
| FFP | 1 μM MB + 44 J/cm$^2$ vis light | none 40 μM quer + 150 μM asc | ≧5 ≧5 | na na | AHF recovery ↑ 73→84% |

(AlPcS$_4$, aluminum phthalocyanine tetrasulfonate; AMT; aminomethyltrimethylpsoralen; MB, methylene blue; quer, quercetin; asc, ascorbate)

presence of 4 mM GSH, the samples are τ-irradiated with 25 Gy in the presence or absence of 1 mM or 2 mM rutin. Plasma potassium is measured after 2 and 7 days of post treatment storage and compared to untreated controls and RBCs treated with AlPcS$_4$ only. (In addition, to examine the effect of rutin addition on K+ leakage with storage after AlPcS$_4$ treatment, one AlPcS$_4$ treated sample which was not gamma-irradiated was stored in the presence of 2 mM rutin). Lymphocyte inactivation and K+ leakage were measured as in a. above.

The addition of τ-irradiation to AlPcS$_4$ treatment increased RBC damage (plasma K+ at 2 days was 75 mM with, and 60 mM without τ-irradiation) unless the flavonoid rutin was present during τ-irradiation and storage (25 mM at 2 days, a 40 mM at 7 days). In addition, when post-treatment storage is in the presence of 2 mM rutin, RBCs show less leakage of potassium after AlPcS$_4$ treatment with or without additional τ-irradiation.

c. PCs: PCs are treated with τ-irradiation at doses of 15, 25 or 50 Gy using a cobalt-60 source in the presence of absence of 1 or 2 mM rutin. Lymphocyte inactivation is determined by $^3$H thymidine uptake after mitogen stimulation as in 1 a. above. Platelet integrity was determined by the aggregation response (initial rate as compared to the untreated control) to 40 µM arachidonic acid and 10 µg/ml ADP at 1 and 3 days after storage.

As in RBCCs, irradiated lymphocytes in PCs retained only 1.5% of their $^3$H thymidine uptake after a 15 Gy exposure and none after 50 Gy and this was independent of the presence of concentration of rutin. Platelet aggregation which decreased with increasing irradiation dosage (90% with 15, 80% with 25 and 70% of the control with 50 Gy after 1 day) was returned to near control levels (95%) by the presence of 2 mM rutin. With 50 Gy of τ-irradiation, lymphocytes were completely inactivated and the rate of aggregation after 3 day storage was 50% of the control in the absence of quenchers and 80% of the control when 2 mM rutin was present during treatment. Thus, quenchers can be used to increase the specificity of τ-irradiation of PCs for lymphocyte inactivation.

2. UVB irradiation of Pcs

PCs from dogs were irradiated with 36 mJ/cm$^2$ UVB (a dose known to prevent HLA alloimmunization; Slichter et al., 1987, *Blood*, 69:414–418) in the presence or absence of 2 mM rutin. Treated platelets were radiolabeled ($^{51}$chromium) and infused. Survival of UV-exposed donor platelets was reduced to 2.5 days when treatment was in the absence of rutin, but survival was the same as in untreated autologous dog platelets (5 days) when irradiation was in the presence of rutin.

It will be appreciated that the instant specification is set forth by way of illustration and not limitation, and that various modifications and changes may be made without departing from the spirit and scope of the present invention.

What is claimed is:

1. A process for transfusing a cell-containing fraction into a donor comprising:

(a) withdrawing a cell-containing fraction from the donor;

(b) treating said cell-containing fraction with a virucidally effective amount of artificial irradiation in the presence of (i) a mixture of at least one quencher compound that quenches type I free radical mediated photodynamic reactions and at least one quencher compound that quenches type II reactive forms of oxygen mediated photodynamic reactions or (ii) a quencher compound that quenches both type I and type II reactions or (iii) a mixture of a quencher compound that quenches both type I and type II reactions and an additional quencher compound; and (c) returning to the donor said treated cell-containing fraction.

2. The process according to claim 1, wherein the irradiation is ultraviolet, gamma-irradiation, x-ray or visible light.

3. The process according to claim 2, wherein the irradiation is UVA, UVB or UVC.

4. The process according to claim 1, wherein the quencher compounds are selected from the group consisting of ascorbate, quercetin, rutin, chrysin, histidine, glutathione, tryptophan, mannitol, glycerol, superoxide dismutase and sodium carpryl N-acetyl tryptophan.

5. The process according to claim 1, wherein the quencher compound that quenches both type I and type II reactions is a flavonoid.

6. The process according to claim 5, wherein the flavonoid is selected from the group consisting of quercetin, chrysin, catechin, rutin, hesperidin and naringin.

7. The process according to claim 1, wherein the cell-containing fraction contains an extracellular or intracellular virus selected from the group consisting of vesicular stomatitis virus, encephalomyocarditis virus, human immunodeficiency virus, hepatitis A virus, hepatitis B virus, non-A, non-B hepatitis virus, adeno-associated virus, M13 and poliovirus.

8. The process according to claim 1, wherein said cell-containing fraction contains red blood cells.

9. The process according to claim 8, wherein said cell-containing fraction contains $\geq 1 \times 10^9$ cells/ml.

10. The process according to claim 9, wherein said cell-containing fraction is selected from the group consisting of whole blood and red cell concentrates.

11. The process according to claim 8, which results in a retention of structural integrity of at least 70% of said red blood cells, and the structural integrity of said red blood cells is ascertained by assessing the mount of hemoglobin released after treatment of said cell-containing fraction with irradiation and said quencher compound, a release of less than 30% of said hemoglobin indicates that the structural integrity of at least 70% of said red blood cells was retained after said treatment.

12. The process according to claim 11, which results in a retention of structural integrity of at least 80% of said red blood cells.

13. The process according to claim 12, which results in a retention of structural integrity of at least 95% of said red blood cells.

14. The process according to claim 1, wherein said cell-containing fraction contains platelets.

15. The process according to claim 14, wherein said cell-containing fraction contains $\geq 1 \times 10^9$ cells/ml.

16. The process according to claim 15, wherein said cell-containing fraction is a platelet concentrate.

17. The process according to claim 14, which results in a retention of structural integrity of at least 70% of said platelets, and the structural integrity of said platelets is ascertained by counting the number of platelets remaining after treatment of said cell-containing fraction with irradiation and said quencher compound, a retention of greater than 70% of said platelets indicates that the structural integrity of at least 70% of said platelets was retained after said treatment.

18. The process according to claim 17, which results in a retention of structural integrity of at least 80% of said platelets.

19. The process according to claim 18, which results in a retention of structural integrity of at least 95% of said platelets.

20. The process according to claim 1, wherein said cell-containing fraction contains at least one coagulation factor.

21. The process according to claim 20, wherein said cell-containing fraction is devoid of cells.

22. The process according to claim 21, wherein said coagulation factor is selected from the group consisting of factors V, VII, VIII, IX, and XI and fibrinogen.

23. The process according to claim 22, wherein said coagulation factor is factor VIII.

24. The process according to claim 20, wherein at least 75% of said coagulation factor is retained after treatment of said cell-containing fraction with irradiation and said quencher compound.

25. The process according to claim 24, wherein at least 85% of said coagulation factor is retained.

26. The process according to claim 25, wherein at least 95% of said coagulation factor is retained.

27. The process according to claim 8, wherein the cell-containing fraction contains an extracellular or intracellular virus selected from the group consisting of vesicular stomatitis virus, encephalomyocarditis virus, human immunodeficiency virus, hepatitis A virus, hepatitis B virus, non-A, non-B hepatitis virus, adeno-associated virus, M13 and poliovirus.

28. The process according to claim 1, wherein the cell-containing fraction is subjected to irradiation and said quencher compound in the presence of an irradiation sensitizer.

29. The process according to claim 28, wherein the irradiation sensitizer is a psoralen.

30. The process according to claim 29, wherein the irradiation is UVA.

31. The process according to claim 29, wherein the psoralen is 4'-aminomethyl-4,5', 8-trimethylpsoralen.

32. The process according to claim 28, wherein the irradiation sensitizer is a brominated hematoporphyrin.

33. The process according to claim 1, wherein either before, after or at the same time as said cell-containing fraction is subjected to said irradiation and said quencher compound, the composition is subjected to at least one different virucidal method.

34. The process according to claim 33, wherein the different virucidal method is selected from the group consisting of heat treatment, pH manipulation, solvent or detergent or solvent and detergent treatment, gamma-irradiation treatment, and formaldehyde treatment.

35. The process according to claim 34, wherein the different virucidal method is solvent or solvent and detergent treatment.

36. The process according to claim 35, wherein the treatment consists of treatment with tri(n-butyl)phosphate and Triton X-100.

37. The process according to claim 28, wherein the cell-containing fraction contains an extracellular or intracellular virus selected from the group consisting of vesicular stomatitis virus, encephalomyocarditis virus, human immunodeficiency virus, hepatitis A virus, hepatitis B virus, non-A, non-B hepatitis virus, adeno-associated virus, M13 and poliovirus.

38. The process according to claim 1, wherein the quencher compound is rutin and wherein the artificial irradiation is selected from the group consisting of ultraviolet, gamma-irradiation, x-ray and visible light.

39. The process according to claim 38, wherein said cell-containing fraction contains red blood cells.

40. The process according to claim 39, wherein said cell-containing fraction is a red blood cell concentrate.

41. The process according to claim 38, wherein said cell-containing fraction contains platelets.

42. The process according to claim 41, wherein said cell-containing fraction is a platelet concentrate.

43. The process according to claim 38, wherein said cell-containing fraction contains coagulation factors.

44. The process according to claim 43, wherein said cell-containing fraction is plasma.

45. The process according to any one of claims 38–44, wherein said process is carried out in the presence of an irradiation sensitizer.

46. The process according to claim 45, wherein the irradiation sensitizer is a psoralen.

47. The process according to claim 46, wherein the irradiation is ultraviolet.

48. The process according to claim 47, wherein the psoralen is 4'-aminomethyl-4,5', 8-trimethylpsoralen.

* * * * *